(12) United States Patent
Duefel et al.

(10) Patent No.: US 12,077,600 B2
(45) Date of Patent: Sep. 3, 2024

(54) ANTI-THYMIDINE KINASE ANTIBODIES

(71) Applicant: Roche Diagnostics Operations, Inc., Indianapolis, IN (US)

(72) Inventors: Hartmut Duefel, Penzberg (DE); Alfred Engel, Penzberg (DE); Frank Kroner, Penzberg (DE); Thomas Meier, Penzberg (DE); Sandra Rutz, Penzberg (DE); Michael Schraeml, Penzberg (DE); Gloria Tabares, Penzberg (DE); Ulrike Kurtkaya, Penzberg (DE); Boris Pinchuk, Penzberg (DE); Christina Zimmermann, Penzberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 996 days.

(21) Appl. No.: 17/069,349

(22) Filed: Oct. 13, 2020

(65) Prior Publication Data

US 2021/0061924 A1 Mar. 4, 2021

Related U.S. Application Data

(63) Continuation of application No. PCT/EP2019/059775, filed on Apr. 16, 2019.

(30) Foreign Application Priority Data

Apr. 18, 2018 (EP) ..................... 18168009

(51) Int. Cl.
| | | |
|---|---|---|
| G01N 31/00 | (2006.01) | |
| C07K 16/40 | (2006.01) | |
| G01N 33/53 | (2006.01) | |
| G01N 33/543 | (2006.01) | |

(52) U.S. Cl.
CPC ....... C07K 16/40 (2013.01); G01N 33/54326 (2013.01); *C07K 2317/92* (2013.01)

(58) Field of Classification Search
None
See application file for complete search history.

(56) References Cited

U.S. PATENT DOCUMENTS

| | | |
|---|---|---|
| 5,221,605 A | 6/1993 | Bard et al. |
| 5,316,757 A | 5/1994 | Sherry et al. |
| 5,342,606 A | 8/1994 | Sherry et al. |
| 5,385,893 A | 1/1995 | Kiefer |
| 5,428,139 A | 6/1995 | Kiefer et al. |
| 5,428,155 A | 6/1995 | Sherry et al. |
| 5,462,725 A | 10/1995 | Kiefer et al. |
| 5,480,990 A | 1/1996 | Kiefer et al. |
| 5,591,581 A | 1/1997 | Massey et al. |
| 5,597,910 A | 1/1997 | Gudibande et al. |
| 5,679,519 A | 10/1997 | Oprandy |
| 5,739,294 A | 4/1998 | Kiefer et al. |
| 5,750,660 A | 5/1998 | Kiefer et al. |
| 5,831,456 A | 11/1998 | Kiefer et al. |
| 9,503,190 B2 | 11/2016 | Yeh et al. |
| 9,606,763 B2 | 3/2017 | Tsukamoto et al. |
| 9,716,942 B2 | 7/2017 | Lippitt et al. |
| 2007/0141650 A1 | 6/2007 | Skog |
| 2010/0111856 A1 | 5/2010 | Gill et al. |
| 2016/0082032 A1 | 3/2016 | Sakamoto et al. |

FOREIGN PATENT DOCUMENTS

| | | | |
|---|---|---|---|
| CN | 102504027 A | 6/2012 | |
| CN | 106556592 A | 4/2017 | |
| JP | 2006526156 A | 11/2006 | |
| WO | 87/06706 A1 | 11/1987 | |
| WO | 90/05296 A1 | 5/1990 | |
| WO | 90/05301 A1 | 5/1990 | |
| WO | 92/14139 A1 | 8/1992 | |
| WO | 95/08644 A1 | 3/1995 | |
| WO | 96/06763 A1 | 3/1996 | |
| WO | 96/24690 A1 | 8/1996 | |
| WO | 96/33411 A1 | 10/1996 | |
| WO | 96/39534 A1 | 12/1996 | |
| WO | 96/40978 A1 | 12/1996 | |
| WO | 96/41175 A1 | 12/1996 | |
| WO | 97/03653 A1 | 2/1997 | |
| WO | 03/002974 A2 | 1/2003 | |
| WO | 2012/107419 A1 | 8/2012 | |
| WO | 2014185528 A1 | 11/2014 | |
| WO | WO-2015094106 A1 * | 6/2015 | ............. C07K 16/40 |
| WO | 2018030946 A1 | 2/2018 | |

OTHER PUBLICATIONS

Blend et al., Labeling anti-HER2/neu Monoclonal Antibodies with 111In and 90Y Using a Bifunctional DTPA Chelating Agent; Cancer Biotherapy & Radiopharmaceuticals; 2003, vol. 18, pp. 355-363.
Briggs et al., synthesis of functionalized fluorescent dyes and their coupling to amines and amino acids; J. Chem. Soc., 1997, pp. 1051-1058.
Camera et al., Comparative biodistribution of indium- and yttrium-labeled B3 monoclonal antibody conjugated to either 2-(p-SCN-Bz)-6-methyl-DTPA (1 B4M-DTPA) or 2-(p-SCN-Bz)-1,4,7,10-tetraazacyclododecane tetraacetic acid (2B-DOTA); 1994, J. Nucl. Med., vol. 21; pp. 640-646.
Camera et al., Nucl. Med. Biol. 20, 1993, pp. 955-962.
Denardo et al., Comparison of 1,4,7, 10-Tetraazacyclododecane-N,N',N", N'"-tetraacetic acid (DOTA)-Peptide-ChL6, a Novel Immunoconjugate with Catabolizable Linker, to 2-Iminothiolane-2-[p-(Bromacetamido)benzyl]-DOTA-ChL6 in Breast Cancer Xenografts; Clinical Cancer Research; 1998, vol. 4. pp. 2483-2490.
Dodeigne et al., Chemiluminescence as diagnostic tool. A review; Talanta, 2000, vol. 51, No. 3, pp. 415-439.

(Continued)

*Primary Examiner* — Lisa V Cook
(74) *Attorney, Agent, or Firm* — Stinson LLP

(57) ABSTRACT

The present invention relates to a novel monoclonal antibody that specifically binds to a conformation dependent epitope on human thymidine kinase 1 (hTK-1; SEQ ID NO:1), to methods for quantifying hTK-1 employing the antibody and to the use of the anti-hTK-1 antibody in quantifying hTK-1.

19 Claims, 5 Drawing Sheets

Specification includes a Sequence Listing.

(56) References Cited

OTHER PUBLICATIONS

Harlow et al., Antibodies: A Laboratory Manual; Biochemical Education, 1989, Vo.. 17, No. 4, 1-page.

Hnatowich et al., The Preparation of DPTA-Coupled Antibodies Radiolabeled with Metallic Radionnuclides: an Improved Method; 1983, Journal of Immunological Methods, vol. 65, pp. 147-157.

Izard et al., An improved method for labeling monoclonal antibodies with samarium-153: use of the bifunctional chelate 2-(p-isothiocyanatobenzyl)-6-methyldiethylenetriaminepentaacetic acid; Bioconjugate Chem.; 1992, vol. 3, No. 4, pp. 346-350.

Knight et al., Occurrence, Mechanisms and Analytical applications of Electrogenerated Chemiluminescence; Analyst. 1994, vol. 119: 879-890.

Kobayashi et al., Evaluation of the in Vivo Biodistribution of Indium-111 and Yttrium-88 Labeled Dendrimer-1B4M-DTPA and Its Conjugation with Anti-Tac Monoclonal Antibody; Bioconjugate Chem.; 1999, vol. 10, pp. 103-111.

Kobayashi et al., Evaluation of the In Vivo Biodistribution of Yttrium-Labeled Isomers of CHX-DTPA-Conjugated Monoclonal Antibodies; J. Nucl. Med.m 1996, Voo. 39, pp. 829-836.

Kukis et al., Optimized Conditions for Chelation of Yttrium-90-DOTA Immunoconjugates; 1998, 7-pages.

Lee et al., Specific Localization, Gamma Camera Imaging, and Intracellular Trafficking of Radiolabelled Chimeric Anti-G(D3) Ganglioside Monoclonal Antibody KM871 in SK-MEL-28 Melanoma Xenografts; Cancer Research, 2001, vol. 61, pp. 4474-4482.

Mardiossian et al., Labeling anti-HER2/neu Monoclonal Antibodies with 111In and 90Y Using a Bifunctional DTPA Chelating Agent; Nucl. Med. Biol. 1993, vol. 20, pp. 65-74.

Meares et al., Conjugation of Antibodies with Bifunctional Chelating Agents: Isothiocyanate and Bromoacetamide Reagents, Methods of Analysis, and Subsequent Addition of Metal Ions'; Oct. 1, 1984—Analytical Biochemistry; vol. 142, 6pp. 8-78.

Meares et al., Macrocyclic chelates of radiometals for diagnosis and therapy; Br. J. Cancer, 1990, vol. 62, Suppl. X, pp. 21-26.

Miederer et al., Pharmacokinetics, Dosimetry, and Toxicity of the Targetable Atomic Generator, (255)Ac-HuM195, in Nonhuman Primates; 2003, 10-pages.

Mitchell et al., Targeting Primary Human Ph+ B-Cell Precursor Leukemia-Engrafted SCID Mice Using Radiolabeled Anti-CD19 Monoclonal Antibodies; 9-pages.

Mirzadeh et al., Radiometal labeling of immunoproteins: covalent linkage of 2-(4-isothiocyanatobenzyl) diethylenetriaminepentaacetic acid ligands to immunoglobulin; Bioconjugate Chem 1; 1990, pp. 59-65.

Nikula et al., A rapid, single vessel method for preparation of clinical grade ligand conjugated monoclonal antibodies; Nuclear Medicine and Biology, vol. 22, Issue 3, Apr. 1995, pp. 387-390.

Nikula et al., Alpha-Emitting Bismuth Cyclohexylbenzyl DTPA Constructs of Recombinant Humanized Anti-CD33 Antibodies: Pharmacokinetics, Bioactivity, Toxicity and Chemistry; The Journal of Nuclear Medicine; 1999, vol. 40, No. 1, 12-pages.

Roselli et al., In Vivo Comparison of CHX-DTPA Ligand Isomers in Athymic Mice Bearing Carcinoma Xenografts; Cancer Biotherapy & Radiopharmaceuticals, 1999, vol. 14, No. 3, 14-pages.

Ruegg et al., Improved in Vivo Stability and Tumor Targeting of Bismuth-labeled Antibody1; Cancer Research, 1990, vol. 50, pp. 4221-4226.

Seeber et al., A Robust High Throughput Platform to Generate Functional Recombinant Monoclonal Antibodies Using Rabbit B Cells from Peripheral Blood; PLOS One; 2014, vol. 9, No. 2, e86184.

H. Sharif et al., Quaternary structures of recombinant, cellular, and serum forms of Thymidine Kinase 1 from dogs and humans; BMC Biochemistry, 2012, vol. 13, No. 12, 10-pages.

Siegel et al., Cancer Statistics, 2013; CA Cancer J Clin, vol. 63, pp. 11-30.

Staffilani et al., Multimetallic Ruthenium(II) Complexes as Electrochemiluminescent Labels; Inorg. Chem. vol. 42, 2003, pp. 7789-7798.

Verel et al., Quantitative 89Zr Immuno-PET for In Vivo Scouting of 90Y-Labeled Monoclonal Antibodies in Xenograft-Bearing Nude Mice; 9-pages.

* cited by examiner

ANTI-THYMIDINE KINASE ANTIBODIES

CROSS-REFERENCE TO RELATED APPLICATION

The present invention claims priority to International Patent Application No. PCT/EP2019/059775 (published as WO2019/201901), filed Apr. 16, 2019, which claims priority to EP Patent Application No. 18168009.1, filed Apr. 18, 2018, both of which are hereby incorporated by reference in their entireties.

The present invention relates to a novel monoclonal antibody that specifically binds to human thymidine kinase 1 (hTK-1; SEQ ID NO:1), to methods for quantifying hTK-1 employing the antibody and to the use of the anti-hTK-1 antibody in quantifying hTK-1.

Despite all progress made in recent decades, cancer is the second leading cause of death (Siegel et al., 2013). Biomarkers are of utmost importance to better understand cancer biology and to better assess important clinically relevant questions such as diagnosis of a malignancy, or detection of recurrence just to mention two key topics.

One class of biomarkers that is of particular interest in the field of oncology is the class of proliferation biomarkers, including Ki-67, proliferating cell nuclear antigen (PCNA) and thymidine kinase (TK-1). Any tumor comprises a relatively high fraction of proliferating cells and a marker of proliferation should be able to identify those proliferating, malignant cells. Literature is available demonstrating that thymidine kinase is quite a useful marker on the tissue level, i.e. if measured by immunohistochemistry.

Serum TK1 activity measurements have been used for monitoring and for prognostic purposes in several different malignant diseases, but primarily in case of leukemia and lymphoma. However, immuno assays for measurement of circulating thymidine kinase from a bodily fluid like serum are scare and immuno assays for serum TK-1 protein are not—yet—widely used in clinical diagnostic routine.

Thymidine kinase 1, (abbreviations: TK1 or TK-1), (ATP: thymidine 5'-phosphotransferase, EC 2.7.1.21) is an enzyme involved in DNA precursor synthesis. The sequence of human thymidine kinase 1 (hTK-1 or hTK1) is known and given in SEQ ID NO:1.

The serum TK1 activity can be measured using a radioactive substrate 1251-dUrd (the PROLIFIGEN® TK-REA, DiaSorin Inc.). A non-radiometric TK1 activity assay (TK LIAISON® assay, DiaSorin Inc.) has become available in recent years. This is a sensitive and robust assay and has provided clinically valuable information in humans and dogs with hematologic malignancies, particularly for monitoring therapy and predicting relapse.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Many attempts have been made to produce useful, sensitive and specific antibodies to hTK-1 over the past decades. However, the antibodies described and available up to date did not meet the requirements for development of a reliable and sensitive immuno assay for measurement of hTK-1 from a bodily fluid sample.

It was therefore the task of the inventors to the present disclosure to develop novel monoclonal antibodies that—once employed in standard immuno assay methods—allow for the reliable detection and quantification of hTK-1 from a bodily fluid sample.

This need is addressed by the present invention by providing the embodiments as defined in the claims.

Surprisingly it has been found and could be shown that a monoclonal antibody to human thymidine kinase 1 (hTK-1; SEQ ID NO:1) that binds to a conformation dependent epitope of hTK-1, but does not bind to a polypeptide consisting of amino acids 194 through 225 of hTK-1 (SEQ ID NO:2), and does not bind to any polypeptide consisting of 15 consecutive amino acids of hTK-1, solves the problem underlying the present disclosure.

SUMMARY OF THE INVENTION

In one embodiment the present disclosure relates to a monoclonal antibody that specifically binds to human thymidine kinase 1 (hTK-1; SEQ ID NO:1) the antibody being characterized in that it
a) binds to a conformation dependent epitope of hTK-1,
b) does not bind to a polypeptide consisting of amino acids 194 through 225 of hTK-1 (SEQ ID NO:2), and
c) does not bind to any polypeptide consisting of 15 consecutive amino acids of hTK-1.

In one embodiment the present disclosure is about an in vitro method for quantifying hTK-1, the method comprising
a) incubating a sample in which hTK-1 shall be quantified with an antibody that specifically binds to human thymidine kinase 1 (hTK-1; SEQ ID NO:1) the antibody being characterized in that it (i) binds to a conformation dependent epitope of hTK-1, (ii) does not bind to a polypeptide consisting of amino acids 194 through 225 of hTK-1 (SEQ ID NO:2), and (iii) does not bind to any polypeptide consisting of 15 consecutive amino acids of hTK-1 of claim 1 or 2, thereby generating a complex between the antibody and hTK-1, and
b) quantifying the complex formed in step a), thereby quantifying hTK-1.

Further the use of an antibody against hTK-1 as disclosed in the present disclosure in quantifying hTK-1 is demonstrated.

DETAILED DESCRIPTION

In a first embodiment the present description relates to a monoclonal antibody that specifically binds to human thymidine kinase 1 (hTK-1; SEQ ID NO:1) the antibody being characterized in that it a) binds to a conformation dependent epitope of hTK-1, b) does not bind to a polypeptide consisting of amino acids 194 through 225 of hTK-1 (SEQ ID NO:2), and c) does not bind to any polypeptide consisting of 15 consecutive amino acids of hTK-1.

Human thymidine kinase 1 is an enzyme consisting of 234 amino acids as shown in SEQ ID NO:1. In the human organism TK-1 is present in various forms like dimers, tetramers and polymers of high molecular weight. These forms seem to depend on the presence of certain molecules, e.g. presence or absence of adenosine triphosphate (ATP); the concentration of the hTK-1 protein itself, the type of the protein, i.e. native or recombinant TK 1; and on the site/location of the protein, i.e. in serum or cytoplasm.

Generally, cytosolic and recombinant human TK1 occurs mainly as tetramers in the presence of ATP or at high concentration, and as dimers in the absence of ATP or at low concentration. The tetramer form of cytosolic and recombinant human TK1 has high TK1 activity whereas the dimer form has lower TK1 activity.

Human serum TK1, in clear contrast, can be in the form of high molecular weight complexes, such as oligomers or comprising such oligomers, having serum TK1 activity and dimer and tetramer forms having very low or even lacking serum TK1 activity.

Many attempts have been made and are described in the prior art, to generate monoclonal antibodies against hTK-1. Some of these antibodies are commercially available like 3B3.E11 from Abcam; EPR3194 and EPR3193, rabbit monoclonal antibodies from Abnova but do not react sufficiently well with serum TK1. These anti-TK1 antibodies have been generated based on human recombinant TK1. It has therefore been postulated (WO 2015/094106) that the generation of monoclonal anti-TK1 antibodies based on human recombinant TK1 is generally inefficient and will typically not produce antiTK1 antibodies capable of binding to the serum form of TK1 at sufficient binding strength.

Contrary to the negative experiences and contrary to the general assumption in the prior art it now was surprisingly found that it is possible to use recombinant hTK-1 as an immunogen in order to obtain the antibody according to the present invention.

The antibodies according to the present invention bind to a conformation dependent epitope, since none of the 15-mer linear peptides, spanning the entire sequence of hTK-1, and shifted by one amino acid, is bound by any of the antibodies disclosed in the present invention.

The overall structure of antibodies comprises of two heavy chains and two light chains, connected by disulfide bonds. The heavy chains and the light chains each consist of one constant domain and one variable domain Binding specificity to an antigen is provided by the variable domains of the light and heavy chains that form the antibody. More specifically, the parts of antibodies that determine their specificity and make contact with a specific ligand are referred to as the complementarity determining regions (CDRs). The CDRs are the most variable part of the molecule and contribute to the diversity of these molecules. There are three CDR regions CDR1, CDR2 and CDR3 in each variable domain, embedded into four framework regions (FWs). As used herein, CDR-HC (or CDR(HC)) depicts a CDR region of a variable heavy chain and CDR-LC (or CDR(LC)) relates to a CDR region of a variable light chain. Similarly, FW-HC (or FW(HC)) depicts a framework region of a variable heavy chain and FW-LC (or FW(LC)) relates to a framework region of a variable light chain.

The term "comprising", as used in accordance with the present invention, denotes that further sequences/components can be included in addition to the specifically recited sequences and/or components. However, this term also encompasses that the claimed subject-matter consists of exactly the recited sequences and/or components.

In those embodiments where the antibody of the invention includes more than the recited amino acid sequence, additional amino acids can be present at either the N-terminal end, or the C-terminal end, or both. Additional sequences can include e.g. sequences introduced e.g. for purification or detection, as discussed in detail herein below. Furthermore, where individual sequences "comprise" the recited sequence, they also can include additional amino acids at either the N-terminal end, or the C-terminal end, or both.

In accordance with the present invention, the antibody specifically binds to human thymidine kinase 1 (hTK-1) of SEQ ID NO:1. It will be appreciated that also in the cases where the antibody of the invention comprises additional amino acids, as detailed above, said antibody necessarily has to specifically bind to hTK-1.

The term "specifically binds" (also referred to herein as "specifically interacts"), in accordance with the present invention, means that the antibody specifically binds only hTK-1, but does not or essentially does not cross-react with a different protein, in particular a different protein of similar structure such as e.g. thymidine kinase 2 (SEQ ID NO:5).

Corresponding methods for analyzing the specificity of an antibody are described e.g. in Harlow & Lane (1988) Antibodies: A Laboratory Manual, Cold Spring Harbor Laboratory Press, and in Harlow & Lane (1999) Using Antibodies: A Laboratory Manual, Cold Spring Harbor Laboratory Press. Non-limiting examples of suitable studies are e.g. binding studies, blocking and competition studies with structurally and/or functionally closely related molecules. These studies can be carried out by methods such as e.g. FACS analysis, flow cytometric titration analysis (FACS titration), surface plasmon resonance (SPR, e.g. with BIAcore®), isothermal titration calorimetry (ITC), fluorescence titration, or by radiolabeled ligand binding assays. Further methods include e.g. Western Blots, ELISA (including competition ELISA)-, RIA-, ECL-, and IRMA-tests.

In context of the present invention, the term "antibody" relates to full immunoglobulin molecules as well as to antigen binding fragments thereof, like, Fab, Fab', F(ab')$_2$, Fv. Furthermore, the term relates to modified and/or altered antibody molecules, as well as to recombinantly or synthetically generated/synthesized antibodies. The term "antibody" also comprises bifunctional antibodies, trifunctional antibodies, fully-human antibodies, chimeric antibodies, and antibody constructs, like single chain Fvs (scFv) or antibody-fusion proteins.

A "Fab fragment" as used herein is comprised of one light chain and the $C_H1$ and variable regions of one heavy chain. The heavy chain of a Fab molecule cannot form a disulfide bond with another heavy chain molecule. A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule. A "F(ab')$_2$ fragment" contains two light chains and two heavy chains containing a portion of the constant region between the $C_H1$ and $C_H2$ domains, such that an interchain disulfide bond is formed between the two heavy chains A F(ab')$_2$ fragment thus is composed of two Fab' fragments that are held together by a disulfide bond between the two heavy chains.

Fab/c fragment contain both Fc and Fab determinants, wherein an "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

The "Fv region" comprises the variable regions from both the heavy and light chains, but lacks the constant regions. "Single-chain Fvs" (also abbreviated as "scFv") are antibody fragments that have, in the context of the present invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. 113 (1994), 269-315.

The term "chimeric antibodies" refers to antibodies that comprise a variable region of a human or non-human species fused or chimerized to an antibody region (e.g., constant region) from another species, either human or non-human (e.g., mouse, horse, rabbit, dog, cow, chicken).

As mentioned above, the term "antibody" also encompasses antibody constructs, such as antibody-fusion proteins, wherein the antibody comprises (an) additional domain(s), e.g. for the isolation and/or preparation of recombinantly produced constructs, in addition to the domains defined herein by specific amino acid sequences.

The antibody of the present invention can be produced such that it is a recombinant antibody, for example a recombinant rabbit antibody, or a hetero-hybrid antibody, yet comprising the CDRs as disclosed and defined in the present invention.

The term "recombinant antibody" includes all antibodies that are prepared, expressed, created or isolated by recombinant means. Recombinant antibodies are e.g. antibodies obtained by B-cell PCR, or antibodies isolated from an animal (e.g., a mouse) that is transgenic for human immunoglobulin genes, antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Recombinant rabbit antibodies as produced by B-cell PCR have variable and constant regions (if present) derived from rabbit germline immunoglobulin sequences. I.e. the direct result of B-cell PCR are the binding relevant fragments of an antibody and the skilled artisan has no problem whatsoever to e.g. construe a full length antibody, a chimeric antibody, or whatever "antibody" that will be desired/required.

The term "hetero-hybrid antibody" refers to an antibody having light and heavy chains that originate from different organisms. For example, an antibody having a human heavy chain associated with a murine light chain is a hetero-hybrid antibody. Examples of hetero-hybrid antibodies include chimeric and humanized antibodies.

The antibody or antigen binding fragment thereof in accordance with the present invention binds a) to a conformation dependent epitope on human thymidine kinase 1 (hTK-1; SEQ ID NO:1), b) does not bind to a polypeptide consisting of amino acids 194 through 225 of hTK-1 (SEQ ID NO:2), and c) does not bind to any polypeptide consisting of 15 consecutive amino acids of hTK-1.

Binding of an anti-hTK-1 antibody to a peptide of SEQ ID NO:2, respectively non-binding to the same, is determined by use of an N-terminally biotinylated peptide of SEQ ID NO:2. Such peptide is bound to a streptavidin coated solid phase and binding, respectively non-binding, is determined according to standard procedures. In essentially the same way binding, respectively non-binding, of an anti-hTK-1 antibody to any polypeptide consisting of 15 consecutive amino acids of hTK-1 is determined. For the latter purpose each 15-mer polypeptide consisting of 15 consecutive amino acids of hTK-1 is synthesized N-terminally biotinylated and antibodies are tested for binding, respectively non-binding. Each peptide is bound to a streptavidin coated solid phase and binding, respectively non-binding, is determined according to standard procedures.

In one embodiment an antibody according to the present invention binds to the same epitope as an antibody comprising variable heavy chain (vHC) of SEQ ID NO:3 and a variable light chain (vLC) of SEQ ID NO:4. Such antibody may be a variant of the specific antibody given and, e.g., may comprise amino acid substitutions, or in the alternative may have a different vHC or a different vLC or both.

The term "substitution", in accordance with the present invention, refers to the replacement of an amino acid with another amino acid. Thus, the total number of amino acids remains the same. The deletion of an amino acid at a certain position and the introduction of one (or more) amino acid(s) at a different position is explicitly not encompassed by the term "substitution". Substitutions, in accordance with the present invention, can be conservative amino acid substitutions or non-conservative amino acid substitutions. The term "conservative amino acid substitution" is well known in the art and refers to the replacement of an amino acid with a different amino acid having similar structural and/or chemical properties. Such similarities include e.g. a similarity in polarity, charge, solubility, hydrophobicity, hydrophilicity, and/or the amphipathic nature of the residues involved. The amino acid substitution is a conservative amino acid substitutions, in case one amino acid of one of the following groups is substituted by another amino acid of the same group: nonpolar (hydrophobic) amino acids include alanine, valine, leucine, isoleucine, proline, phenylalanine, tyrosine, tryptophan, and methionine; polar neutral amino acids include glycine, serine, threonine, cysteine, asparagine, and glutamine; positively charged (basic) amino acids include arginine, lysine, and histidine; and negatively charged (acidic) amino acids include aspartic acid and glutamic acid.

The "binding affinity" of an antibody measures the strength of interaction between an epitope on the target antigen and the binding site of the antibody according to the following equation:

$$KD = kd/ka$$

wherein:
KD=dissociation equilibrium constant [M]
kd=dissociation rate constant [$s^{-1}$]
ka=association rate constant [$M^{-1} s^{-1}$]

Further relevant parameters for the binding affinity of an antibody are as follows:
t/2=dissociation complex half-life=ln2/kd/60 [min]
Rmax=response maximum of analyte [RU]
MR: Molar Ratio=ratio of response maximum (Rmax) of analyte In one embodiment a monoclonal antibody to hTK-1 as disclosed herein above binds to hTK-1 with a t/2-diss at 37° C. of 10 minutes or longer.

In one embodiment the monoclonal antibody according to the present disclosure is characterized in that it has a binding affinity to hTK-1 of $10^{-9}$ M or better. In one embodiment the monoclonal antibody according to the present disclosure is characterized in that it has a binding affinity to hTK-1 of $5 \times 10^{-10}$ M or better, or of $2 \times 10^{-10}$ M or better. The antibodies known from the prior art either have not such good affinity or bind to a linear epitope on hTK-1 or both.

Several very good monoclonal antibodies that specifically bind to human thymidine kinase 1 (hTK-1; SEQ ID NO:1) each such antibody being characterized in that it a) binds to a conformation dependent epitope of hTK-1, b) does not bind to a polypeptide consisting of amino acids 194 through 225 of hTK-1 (SEQ ID NO:2), and c) does not bind to any polypeptide consisting of 15 consecutive amino acids of hTK-1 were produced according to the methods disclosed in the Examples section. Surprisingly all three exemplary antibodies bind to a very similar or the same epitope.

Without wanting to be bound to the theory, it would appear that conformational epitope bound by the antibody according to the present invention is absolutely key in establishing a sensitive immunoassay useful in clinical routine. Now that this crucial epitope has been identified it will be quite easy to find other monoclonal antibodies binding to this epitope. Such antibodies can easily be created following the procedures disclosed herein or by modifying the sequences of the antibodies disclosed herein.

It has surprisingly been found that all three antibodies bind to the same epitope. Due to their way of generation binding of these recombinant rabbit monoclonal antibodies is best defined via the sequences obtained in the B-cell PCR, i.e. the part of the heavy chain variable domain and the light chain variable domain obtained via B-cell PCR. MAB 6C6 has been chosen as a prototype antibody for definition of the common epitope. MAB 6C6 is characterized by a heavy chain variable domain of SEQ ID NO:3 and a light chain variable domain of SEQ ID NO:4.

In one embodiment, the invention provides antibodies that bind to the same epitope on human TK-1 as the monoclonal antibody of the invention or a binding fragment thereof having a heavy chain variable domain of SEQ ID NO:3 and a light chain variable domain of SEQ ID NO:4. Antibodies that bind to the same epitope on hTK-1 are antibodies that compete for binding to hTK-1 with an antibody having a heavy chain variable domain of SEQ ID NO:3 and a light chain variable domain of SEQ ID NO:4.

Such competing antibodies can be identified based on their ability to compete with monoclonal rabbit antibody MAB 6C6, i.e. an antibody comprising a heavy chain variable domain of SEQ ID NO:3 and a light chain variable domain of SEQ ID NO:4, in standard hTK-1 binding assays. For example, BIAcore analysis, ELISA assays or flow cytometry may be used to demonstrate competition with a monoclonal antibody or a binding fragment thereof having a heavy chain variable domain of SEQ ID NO:3 and a light chain variable domain of SEQ ID NO:4.

The ability of a test antibody to inhibit the binding of, monoclonal rabbit antibody MAB 6C6 to human TK-1 demonstrates that the test antibody can compete with monoclonal rabbit antibody MAB 6C6 for binding to and thus binds to the same epitope on hTK-1 as monoclonal rabbit antibody MAB 6C6.

As mentioned, several different competition assays may be used to identify an antibody that competes with rabbit monoclonal antibody MAB 6C6 for a binding fragment thereof having a heavy chain variable domain of SEQ ID NO:3 and a light chain variable domain of SEQ ID NO:4.

In an exemplary competition assay, immobilized hTK-1 is incubated in a solution comprising a first labeled antibody that binds to hTK-1 (e.g., an anti-hTK-1 monoclonal antibody or a binding fragment thereof having a heavy chain variable domain of SEQ ID NO:3 and a light chain variable domain of SEQ ID NO:4) and a second unlabeled antibody that is being tested for its ability to compete with the first antibody for binding to hTK-1. The second antibody may be present in a hybridoma supernatant. As a control, immobilized hTK-1 is incubated in a solution comprising the first labeled antibody but not the second unlabeled antibody. After incubation under conditions permissive for binding of the first antibody to hTK-1, excess unbound antibody is removed, and the amount of label associated with immobilized hTK-1 is measured. If the amount of label associated with immobilized hTK-1 is substantially reduced in the test sample relative to the control sample, then that indicates that the second antibody is competing with the first antibody for binding to hTK-1. See, e.g., Harlow et al. Antibodies: A Laboratory Manual. Ch.14 (Cold Spring Harbor Laboratory, Cold Spring Harbor, NY, 1988).

Binding properties of an antibody, e.g., of an anti-hTK-1 antibody, are best determined via real time biosensor-based molecular interaction measurements, like surface plasmon resonance spectroscopy, for which Biacore technology became a synonym. In the Biacore system antibodies can also be analyzed for competitive binding to the same epitope (i.e. for binding to an identical epitope or an overlapping epitope). Experimental details are given in Example 3 and kinetic data are shown in Table 1. In one embodiment the competition experiment to characterize an antibody for binding to the conformation dependent epitope as identified herein is performed on the BIAcore instrument as described in the Examples section.

Several non-automated assays for measurement of the hTK-1 protein are available. Probably the assay with most reach is Arocell's hTK-1 assay which is based on a microtiter plate format requiring several manual handling steps and quite long incubation times. However, as mentioned above—most likely due to lack of appropriate antibodies—no immunoassay for hTK-1 running on an automated immunoassay analyzer is available to date. The antibody according to the present invention, however, overcomes this problem. It can be used with great advantage in the in vitro measurement of hTK-1.

The present disclosure in one embodiment relates an in vitro method for quantifying hTK-1, the method comprising: a) incubating a sample in which hTK-1 shall be quantified with an antibody that specifically binds to human thymidine kinase 1 (hTK-1; SEQ ID NO:1) the antibody being characterized in that it (i) binds to a conformation dependent epitope of hTK-1, (ii) does not bind to a polypeptide consisting of amino acids 194 through 225 of hTK-1 (SEQ ID NO:2), and (iii) does not bind to any polypeptide consisting of 15 consecutive amino acids of hTK-1 of claim 1 or 2, thereby generating a complex between the antibody and hTK-1, and b) quantifying the complex formed in step a), thereby quantifying hTK-1.

Examples of immunoassays which can utilize the antibodies of the invention are immunoassays in either a direct or indirect format. Examples of such immunoassays are the enzyme linked immunosorbent assay (ELISA), enzyme immunoassay (EIA), radioimmunoassay (RIA), or immuno assays based on detection of luminescence, fluorescence, chemiluminescence or electrochemiluminescence.

In one embodiment a sandwich immunoassay is employed in the measurement of hTK-1.

Also disclosed herein is an in vitro method for quantifying hTK-1, the method comprising a) incubating a sample in which hTK-1 shall be quantified with a first antibody which is an antibody according to the present disclosure, and a second antibody to hTK-1, thereby generating a sandwich complex between the first antibody, hTK-1 and the second antibody, b) quantifying the sandwich complex formed in step a), thereby quantifying hTK-1.

Interestingly the monoclonal antibody according to the present invention can be used for detection of hTK-1 as present in a serum or plasma sample either with pretreatment of such sample or without pretreatment. This means that the antibody of the present invention also binds oligomeric hTK-1 as present in a serum or plasma sample. In one embodiment the present invention relates to the use of an antibody according to the present invention in the detection of hTK-1, wherein the sample is not pretreated with a reducing agent.

In the prior art, usually a serum or plasma sample is pretreated in order to generate the tetrameric and enzymatically highly active form of hTK-1. The pretreatment of a sample and the measurement of hTK-1 from such pretreated sample represents a very attractive method, since this way e.g. a very good correlation to hTK-1 enzymatic activity can be achieved.

The selection of an appropriate pretreatment reagent is fully within the capabilities of a person skilled in the art. Such pretreatment reagent will at least comprise a reducing agent in order to transform oligomeric hTK-1 into tetrameric hTK-1. As described e.g. by Sharif et al., (BMC Biochemistry (2012), 13:12) it is easy to assess via gel filtration experiments whether the reducing agent has been effective and hTK-1 is—after treatment—primarily present as a tetramer. Several different reducing reagents are at stake for the skilled artisan, e.g. dithiothreitol (DTT), dithioerythritol (DTE), or dithiobutylamin (DTBA). The concentration of the pretreatment reagent will in addition be chosen such way that either after an appropriate time of incubation or after a dilution step it will not negatively impact any antibody used to measure the hTK-1 protein. In case dithiobutylamin (DTBA) is used as a reducing agent an appropriate final concentration in the sample pretreatment step (the mixture of sample and pretreatment reagent) is in the range of 5 mM. After pre-dilution, and/or addition of an agent blocking DTT, and/or by way of dilution with a buffer comprising a first antibody, the concentration of DTT in oxidized form preferably is 1.5 mM or below. This way there is no effect of the reducing agent on any of the immunological reagents used.

As described above, ATP stabilizes the tetrameric form of hTK-1. The latter function of ATP makes it an attractive additive to, e.g., the pretreatment buffer. In one embodiment the pretreatment buffer comprises a reducing agent as discussed above and ATP. The concentration of ATP in the sample pretreatment step should not be below 1.25 mM. A good choice for the ATP concentration in the pretreatment step will be in the range from 2 mM to 20 mM.

In one embodiment the present disclosure relates to an in vitro method for quantifying hTK-1, the method comprising a) incubating a sample in which hTK-1 shall be quantified with a pre-treatment solution comprising a reducing agent and ATP, b) incubating the pre-treated sample obtained in step a) with an antibody according to the present invention, thereby generating a complex between the antibody and hTK-1, c) quantifying the complex formed in step b), thereby quantifying hTK-1.

Sandwich immunoassays are broadly used in the detection of an analyte of interest. In such assay the analyte is "sandwiched" in between a first antibody and a second antibody. By appropriate means such sandwich complex is measured and the analyte thereby quantified.

In one embodiment the present disclosure relates to an in vitro method for quantifying hTK-1, the method comprising a) incubating a sample in which hTK-1 shall be quantified with a pre-treatment solution comprising a reducing agent and ATP b) incubating the pre-treated sample obtained in step a) with a first antibody which is an antibody of according to the present invention, and a second antibody to hTK-1, thereby generating a sandwich complex between the first antibody, hTK-1 and the second antibody, c) quantifying the sandwich complex formed in step b), and thereby quantifying hTK-1.

In one embodiment the method of the present invention is practiced in a sandwich assay format.

In a typical sandwich-type assay, a first antibody bound to the solid phase or capable of binding thereto and a detectably-labeled second antibody each bind to the analyte at different and non-overlapping epitopes. The first analyte-specific binding agent (e.g. an antibody) is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 37° C. inclusive) to allow for binding between the first or capture antibody and the corresponding antigen. Following the incubation period, the solid phase, comprising the first or capture antibody and bound thereto the antigen can be washed, and incubated with a secondary or labeled antibody binding to another epitope on the antigen. The second antibody is linked to a reporter molecule which is used to indicate the binding of the second antibody to the complex of first antibody and the antigen of interest.

An extremely versatile alternative sandwich assay format includes the use of a solid phase coated with the first partner of a binding pair, e.g. paramagnetic streptavidin-coated microparticles. Such microparticles are mixed and incubated with an analyte-specific binding agent bound to the second partner of the binding pair (e.g. a biotinylated antibody), a sample suspected of comprising or comprising the analyte, wherein said second partner of the binding pair is bound to said analyte-specific binding agent, and a second analyte-specific binding agent which is detectably labeled, e.g. with an electrochemiluminescent label as used herein. As obvious to the skilled person these components are incubated under appropriate conditions and for a period of time sufficient for binding the labeled antibody via the analyte, the analyte-specific binding agent (bound to) the second partner of the binding pair and the first partner of the binding pair to the solid phase microparticles. As appropriate such assay may include one or more washing step(s).

In one embodiment the present disclosure relates to a sandwich assay wherein either a first or a second antibody is bound to a solid phase or capable of binding to a solid phase and wherein either a second or a first antibody is detectably labeled, respectively, and wherein at least one of these antibodies is an antibody as disclosed in the present invention.

Usually a sandwich assay requires that capture and detection antibody bind to different, non-overlapping epitopes on an analyte of interest. In the case of serum/plasma hTK-1 preferably the tetrameric form of the enzyme, generated as described above, is measured. In a sandwich assay method for quantification of hTK-1 in one embodiment an antibody according to the present invention is used in combination with an antibody binding to an epitope on the C-terminal part of hTK-1 as represented by the amino acids ranging from position 195 to the C-terminus, i.e. position 234 (SEQ ID NO:5), or an antibody binding to an epitope comprised in the polypeptide consisting of the amino acids ranging from position 195 to position 225 (SEQ ID NO:2). In one embodiment the antibody according to the present invention and an antibody binding to an epitope comprised in amino acids 211 to 230 (SEQ ID NO:6) of hTK-1 are used in a sandwich assay for measurement of hTK-1.

As could be shown by the inventors according to the present invention, it is even possible to use an antibody according to the present invention for both, i.e. as a capture antibody as one part of the sandwich complex as well as a detection antibody one other part of the sandwich complex. In one embodiment the quantification of hTK-1 thus is performed by a sandwich assay using an antibody according to the present invention both as a capture as well as a detection antibody.

In the sandwich immunoassay method for quantitation of hTK-1 at least one antibody to hTK-1 comprises a detectable label.

The term detectably labeled encompasses labels that can be directly or indirectly detected.

Directly detectable labels either provide a detectable signal or they interact with a second label to modify the detectable signal provided by the first or second label, e.g. to give FRET (fluorescence resonance energy transfer). Labels such as fluorescent dyes and luminescent (including chemiluminescent and electrochemiluminescent) dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling. In one embodiment detectably labeled refers to a label providing or inducible to provide a detectable signal, i.e. to a fluorescent label, to a luminescent label (e.g. a chemiluminescent label or an electrochemiluminescent label), a radioactive label or a metal-chelate based label, respectively.

Numerous labels (also referred to as dyes) are available which can be generally grouped into the following categories, all of them together and each of them representing embodiments according the present disclosure:

(a) Fluorescent Dyes

Fluorescent dyes are e.g. described by Briggs et al "Synthesis of Functionalized Fluorescent Dyes and Their Coupling to Amines and Amino Acids," J. Chem. Soc., Perkin-Trans. 1 (1997) 1051-1058).

Fluorescent labels or fluorophores include rare earth chelates (europium chelates), fluorescein type labels including FITC, 5-carboxyfluorescein, 6-carboxy fluorescein; rhodamine type labels including TAMRA; dansyl; Lissamine; cyanines; phycoerythrins; Texas Red; and analogs thereof. The fluorescent labels can be conjugated to an aldehyde group comprised in target molecule using the techniques disclosed herein. Fluorescent dyes and fluorescent label reagents include those which are commercially available from Invitrogen/Molecular Probes (Eugene, Oregon, USA) and Pierce Biotechnology, Inc. (Rockford, Ill.).

(b) Luminescent Dyes

Luminescent dyes or labels can be further subcategorized into chemiluminescent and electrochemiluminescent dyes.

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 (2000) 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescense is triggered by a voltage imposed on a working electrode at a particular time and in a particular manner. The light produced by the label is measured and indicates the presence or quantity of the analyte. For a fuller description of such ECL techniques, reference is made to U.S. Pat. Nos. 5,221,605, 5,591,581, 5,597,910, PCT published application WO 90/05296, PCT published application WO92/14139, PCT published application WO90/05301, PCT published application WO96/24690, PCT published application US95/03190, PCT application US97/16942, PCT published application US96/06763, PCT published application WO95/08644, PCT published application WO96/06946, PCT published application WO96/33411, PCT published application WO87/06706, PCT published application WO96/39534, PCT published application WO96/41175, PCT published application WO96/40978, PCT/US97/03653 and U.S. patent application Ser. No. 08/437,348 (U.S. Pat. No. 5,679, 519). Reference is also made to a 1994 review of the analytical applications of ECL by Knight, et al. (Analyst, 1994, 119: 879-890) and the references cited therein. In one embodiment the method according to the present description is practiced using an electrochemiluminescent label.

Recently also Iridium-based ECL-labels have been described (WO2012107419(A1)).

In one embodiment the directly detectable label is a chemiluminescent or an electrochemiluminescent label. The light produced by the label is measured and directly or indirectly indicates the presence or quantity of the analyte.

(c) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(d) Metal-chelate complexes suitable as labels for imaging and therapeutic purposes are well-known in the art (US 2010/0111856; U.S. Pat. Nos. 5,342,606; 5,428, 155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998)

2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

It is a puzzling finding that despite the fact that hTK-1 is known since decades and despite many, many attempts to produce good immuno assays, there still is no high quality antibody to hTK-1 available that binds to a conformational epitope and is useful in the sensitive detection of hTK-1. Without wanting to be bound to the theory, but, one could imagine that this lack/failure has to do with the fact the hTK-1 may to some extent be blocked by the antibodies induced by immunization. It should not be forgotten that standard hybridoma technology relies on the HAT-medium (hypoxanthine-aminopterin-thymidine) to select hybridomas, i.e., hybridomas must be able to use the thymidine that is added to the selection medium in order to overcome the poisonous effect of aminopterin. The hTK-1 monoclonal antibodies now successfully produced have been obtained via the B-cell PCR technology. In the B-cell PCR technology no HAT medium is used and blocking of hTK-1 by the antibody produced via this technology may be less relevant or completely irrelevant In the Examples shown in the corresponding section of the present disclosure, rabbits have been used as experimental animals, immunized with hTK-1, and their B-cells used in the rabbit B-cell PCR technology. As obvious, the B-cell PCR technology can also be used for other experimental animals, like mice, or can be established in analogy for other experimental animals if need should arise. Thus, while B-cell PCR in rabbits represents one embodiment, the use of the B-cell PCR technology for generating anti-hTK-1 antibodies is not limited to this species.

In one embodiment the antibody to hTK-1 according to the present invention is obtained by B-cell PCR technology.

As described in much detail herein above the antibodies to HTK-1 as disclosed in the present invention can be used with great advantage in the detection of hTK-1. Thus in one embodiment the present invention relates to the use of an antibody as disclosed herein in quantifying hTK-1.

As obvious to the skilled artisan it will be advantageous to use an antibody according to the present invention in a method for detection of hTK-1.

In one embodiment the present disclosure relates to a method of detecting hTK-1 in a sample, the method comprising the steps of: a) contacting the sample with an anti-hTK-1 antibody according to the present disclosure for a time and under conditions sufficient for the formation of an anti-hTK-1 antibody/hTK-1 complex; and b) measuring the anti-hTK-1 antibody/hTK-1 complex, wherein the amount of that complex is indicative for the concentration of hTK-1 in the sample. The terminology "/" e.g. in "anti-hTK-1 antibody/hTK-1 complex" is used in order to indicate that a non-covalent complex is formed between the anti-hTK-1 antibody on the one hand and the hTK-1 on the other hand.

In one embodiment the present invention relates to a method of detecting hTK-1 in a sample comprising the steps of: a) contacting the sample with a first antibody to hTK-1 and a second antibody to hTK-1, wherein the second antibody is detectably labeled, for a time and under conditions sufficient to form a first anti-hTK-1 antibody/hTK-1/second anti-hTK-1 antibody complex; and b) measuring the complex formed in (a), wherein the amount of that complex is indicative for the concentration of hTK-1 in the sample and wherein either the first or the second antibody is an antibody according to the present invention.

As obvious to the skilled artisan the sample can be contacted with the first and the second antibody in any desired order, i.e. first antibody first, the second antibody; second antibody first than first antibody, or simultaneously, for a time and under conditions sufficient to form a first anti-hTK-1 antibody/hTK-1/second anti-hTK-1 antibody complex.

As the skilled artisan will readily appreciate it is nothing but routine experimentation to establish the time and conditions that are appropriate or that are sufficient for the formation of a complex either between the specific anti hTK-1 antibody and the hTK-1 antigen/analyte (=anti-hTK-1 antibody/hTK-1 complex) or the formation of the secondary or sandwich complex comprising the first antibody to hTK-1, the hTK-1 (the analyte) and the second anti-hTK-1 antibody complex (=first anti-hTK-1 antibody/hTK-1/second anti-hTK-1 antibody complex).

The detection of the anti-hTK-1 antibody/hTK-1 complex can be performed by any appropriate means. The person skilled in the art is absolutely familiar with such means/methods.

The term "sample" or "sample of interest" or "test sample" are used interchangeably herein. The sample is an in vitro sample, it will be analyzed in vitro and not transferred back into the body. Examples of samples include but are not limited to fluid samples such as blood, serum, plasma, synovial fluid, urine, saliva, and lymphatic fluid, or solid samples such as tissue extracts, cartilage, bone, synovium, and connective tissue. In one embodiment the sample is selected from blood, serum, plasma, synovial fluid and urine. In one embodiment the sample is selected from blood, serum and plasma. In one embodiment the sample is serum or plasma.

The term "reference sample" as used herein, refers to a sample which is analyzed in a substantially identical manner as the sample of interest and whose information is compared to that of the sample of interest. A reference sample thereby provides a standard allowing for the evaluation of the information obtained from the sample of interest. A reference sample may be derived from a healthy or normal tissue, organ or individual, thereby providing a standard of a healthy status of a tissue, organ or individual. Differences between the status of the normal reference sample and the status of the sample of interest may be indicative of the risk of disease development or the presence or further progression of such disease or disorder. A reference sample may be derived from an abnormal or diseased tissue, organ or individual thereby providing a standard of a diseased status of a tissue, organ or individual. Differences between the status of the abnormal reference sample and the status of the sample of interest may be indicative of a lowered risk of disease development or the absence or bettering of such disease or disorder The terms "elevated" or "increased" level of an indicator refer to the level of such indicator in the sample being higher in comparison to the level of such indicator in a reference or reference sample. E.g. a protein that is detectable in higher amounts in a fluid sample of one individual suffering from a given disease than in the same fluid sample of individuals not suffering from said disease, has an elevated level.

In certain embodiments a sandwich will be formed comprising a first antibody to hTK-1, the hTK-1 (analyte) and the second antibody to hTK-1, wherein the second antibody is detectably labeled.

In one embodiment a sandwich will be formed comprising a first antibody to hTK-1, the hTK-1 (analyte) and the second antibody to hTK-1, wherein the second antibody is detectably labeled and wherein the first anti-hTK-1 antibody is capable of binding to a solid phase or is bound to a solid phase.

In one embodiment the anti-hTK-1 antibody disclosed in the present invention is used in an immunoassay to measure hTK-1. In one embodiment the anti-hTK-1 antibody disclosed herein above is used in a sandwich-type immunoassay. In one embodiment the anti-hTK-1 antibody disclosed in the present invention is used as a detection antibody. In one embodiment the anti-hTK-1 antibody as disclose herein is detectably labeled with a luminescent dye, especially a chemiluminescent dye or an electrochemiluminescent dye.

These and other embodiments are disclosed and encompassed by the description and Examples of the present invention. Further literature concerning any one of the methods, uses and compounds to be employed in accordance with the present invention may be retrieved from public libraries and databases, using for example electronic devices. For example, the public database "Medline", available on the Internet, may be utilized, for example in the World Wide Web under ncbi.nlm nih.gov/PubMed/medline.html. Further databases and addresses available in the World Wide Web, such as ncbi.nlm.nih.gov/, fmi.ch/biology/research_tools.html,tigr.org/, or infobiogen.fr/, are known to the person skilled in the art and can also be obtained using the address in the World Wide Web under lycos.com.

Unless otherwise defined, all technical and scientific terms used herein have the same meaning as commonly understood by one of ordinary skill in the art to which this invention belongs. In case of conflict, the patent specification, including definitions, will prevail.

All amino acid sequences provided herein are presented starting with the most N-terminal residue and ending with the most C-terminal residue (N→C), as customarily done in the art, and the one-letter or three-letter code abbreviations as used to identify amino acids throughout the present invention correspond to those commonly used for amino acids.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 8, 5 and 1 is clearly and unambiguously envisaged in view of the claim structure. The same applies for example to the combination of claims 8, 7 and 2, etc..

Certain aspects of the invention are also illustrated by way of the attached figures.

Figure 4:
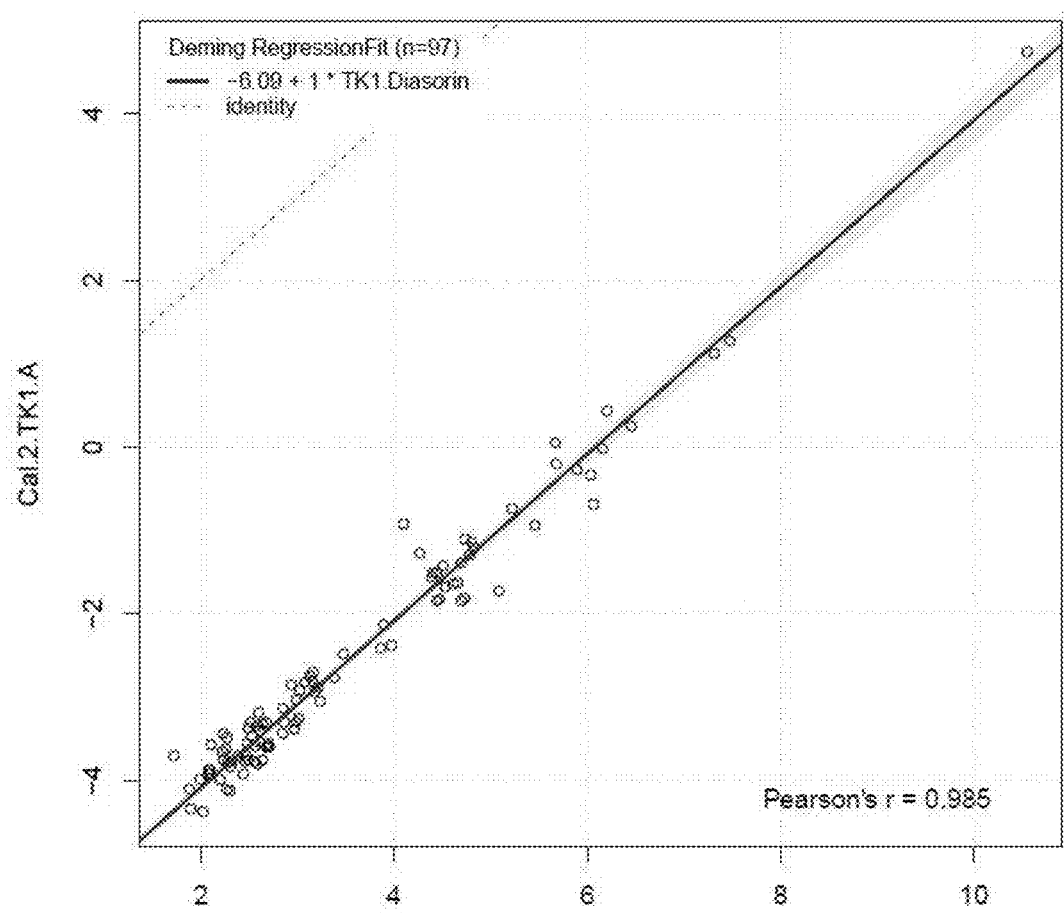
FIGS. 4A and 4B: Method comparison
Figure 4:
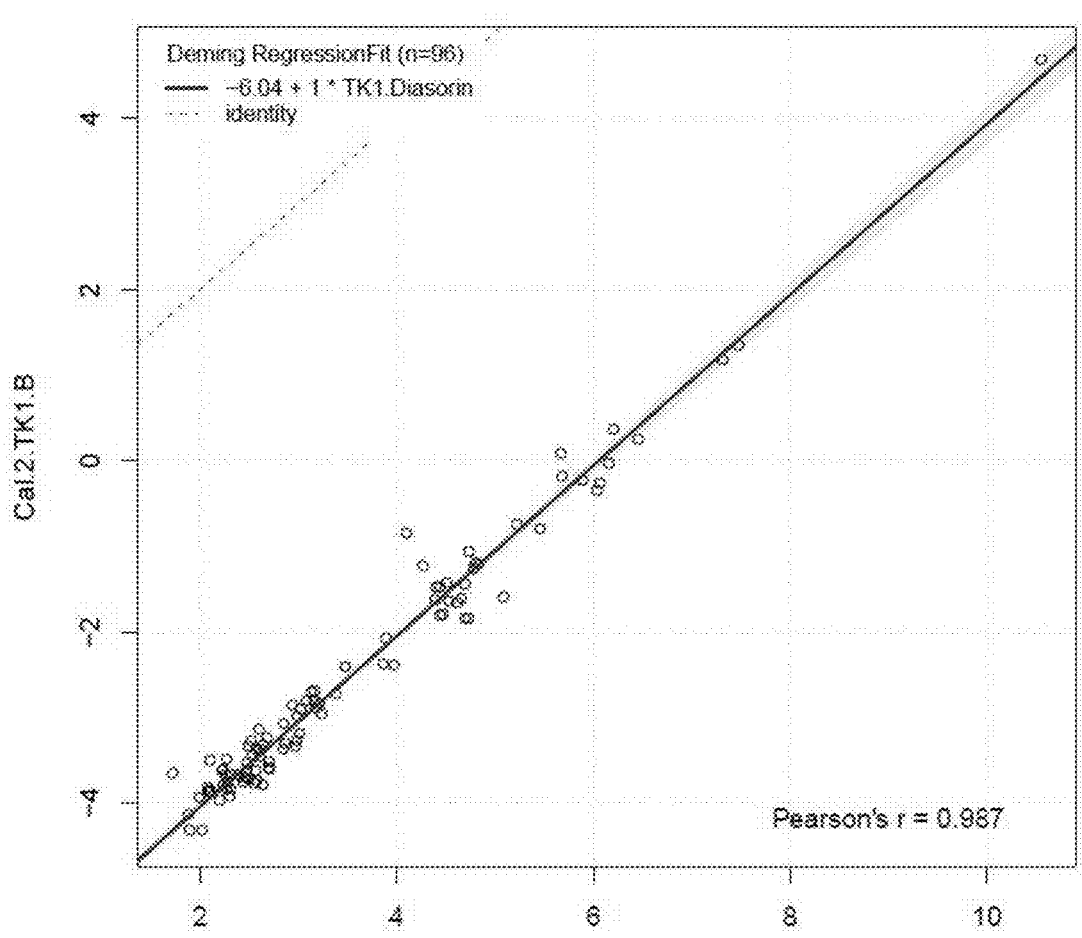

The Deming Regression Fit is shown for both the correlation between the LIAISON® Thymidine Kinase (activity) assay data x-axis and the immunoassay prototype A) y-axis of FIG. 4A and prototype B) y-axis of FIG. 4B, respectively.

The following Examples illustrate the invention:

Example 1: Materials & General Methods

Recombinant DNA Techniques

Standard methods were used to manipulate DNA as described in Sambrook, J. et al., Molecular Cloning: A laboratory manual; Cold Spring Harbor Laboratory Press, Cold Spring Harbor, New York, 1989. The molecular biological reagents were used according to the manufacturer's instructions.

DNA Sequence Determination

DNA sequences were determined by double strand sequencing performed at Microsynth AG (Balgach, Switzerland).

DNA and Protein Sequence Analysis and Sequence Data Management

Vector NT1 Advance suite version 11.5.0 was used for sequence creation, mapping, analysis, annotation and illustration.

Protein Chemistry and Labeling Techniques

Standard protein chemistry and labeling techniques are provided e.g. in Hermanson, G. "Bioconjugate Techniques" 3rd Edition (2013) Academic Press.

Bioinformatics

Bioinformatics methods are provided in e.g. Keith J. M. (ed.) "Bioinformatics" Vol. I and Vol. II, Methods in Molecular Biology Vol. 1525 and Vol. 1526 (2017) Springer, and in Martin, A. C. R. & Allen, J. "Bioinformatics Tools for Analysis of Antibodies" in: Dübel S. & Reichert J. M. (eds.) "Handbook of Therapeutic Antibodies" Wiley-VCH (2014).

Electrochemiluminescent Immunoassays

Immunoassays and related methods are provided in e.g. Wild D. (ed.) "The Immunoassay Handbook" 4th Edition (2013) Elsevier. Ruthenium complexes as electrochemiluminescent labels are provided in e.g. Staffilani M. et al. Inorg. Chem. 42 (2003) 7789-7798. Typically, for the performance of electrochemiluminescence (ECL) based immunoassays an Elecsys 2010 analyzer or a successor system was used, e.g. a Roche analyzer (Roche Diagnostics GmbH, Mannheim Germany) such as E170, cobas e 601 module, cobas e 602 module, cobas e 801 module, and cobas e 411, and Roche Elecsys assays designed for these analyzers, each used under standard conditions, if not indicated otherwise.

Example 2: Generation of Anti-Htk-1 Antibodies

Many attempts have been first made to produce anti-hTK-1 monoclonal antibodies in mice according to standard protocols. In these experiments also a variety of immunogens (recombinant hTK-1 produced in *E. coli*; recombinant hTK-1 produced in HEK-cells; several peptide immunogens) has been used. Only very few monoclonal antibodies were obtained this way and none of the antibodies obtained in these initial experiments showed good binding to TK-1 as comprised in a human serum sample.

In the finally successful attempt for the generation of anti-hTK1 antibodies rabbits have been used as experimental animals Immunization:

For the generation of antibodies against the human thymidine kinase (hTK1), rabbits were immunized with rec hTK1 derived from *E. coli* or with rec native hTK1 derived from HEK293 cells. All rabbits were subjected to repeated immunizations. In the first month the animals were immunized weekly. From the second month onward the animals were immunized once per month. For the first immunization 500 µg rec hTK1 (*E. coli* or HEK293) was dissolved in 1 mL 0,9% (w/v) NaCl and was emulsified in 3.5 ml CFA, for all following immunizations 1.75 mL IFA was used instead of CFA. The development of titers was evaluated on days 45 and 105 after start of the immunization. When titers against the immunogen were detectable by ELISA, antibodies were obtained by B-cell cloning as described below. For the production of full-length rabbit IgG the heavy and light chain coding plasmids, derived from the recombinant IgG cloning process were used for transient transfection of HEK293 cells.

Development and expression of monoclonal antibodies against hTK1 by B-cell PCR technology:

The antibodies against the recombinant human thymidine kinase (hTK1) were obtained using the B-cell PCR method according to Seeber et al. (2014), PLoS One 4, 9(2). PBMCs and B-cells for the single cell deposition were prepared from peripheral blood derived from immunized rabbits at different time points. The individual hTK1 rabbit antibodies were finally recombinantly expressed in HEK293 cells. For the production of full-length rabbit anti hTK1 IgG, the heavy and light chain coding plasmids, derived from the recombinant IgG cloning process were used for transient transfection of HEK293 cells. HEK293 cells were grown in a shaking device at 125 rpm in F17-medium (Gibco) at 37° C. in an atmosphere containing 8% $CO_2$. Cells were split the day before transfection and seeded at a density of 0.7-0.8×$10^6$ cells/ml. On the day of transfection, 1-1.5×$10^6$ HEK293 cells in a volume of 2 ml were transfected with 0.5 mg heavy chain plasmid plus 0.5 mg light chain plasmid, suspended in 80 ml OptiMEMH medium (Gibco) and supplemented with 1 ml PEIpro transfection reagent (Polyplus-Transfection) in 48-well deep well plates. Cultures were incubated for 7 days at 180 rpm at 37° C. and in 8% CO2. After 7 days of incubation the culture supernatants were harvested and analyzed for antibody content and specificity.

Initial testing of recombinant antibodies for anti-hTK-1 binding:

Binding to hTK-1 was first tested in an ELISA format. To this end, the biotinylated variant of the recombinant native hTK1 (derived from HEK293) was coupled to streptavidin as comprised in the wells of a streptavidin pre-coated 96-well microtiter plate (MTP). The biotinylated protein was immobilized in the wells of the MTP 50 µl with a concentration of the biotinylated hTK-1 of 250 ng/mL. 30 µl of the transfection supernatant of each antibody was added to the wells of the MTP and incubated for 30 min at room temperature. After washing, the bound antibody was detected with a HRP-labeled F(ab')2 goat anti-rabbit $Fc_\gamma$ fragment (Dianova) and ABTS (Roche) as the substrate.

This way the four recombinant rabbit antibodies termed 4H4; 4H11, 6C6 and 23C11, respectively, have been obtained.

For all the recombinant rabbit antibodies the sequences of the variable light chains as well as of the binding-relevant part of the heavy chain (i.e. the variable heavy chain comprising the three CDRs, the framework regions and part of constant region 1) were determined according to standard procedures.

```
hTK1, Klon 6C6, heavy chain:
                                       (SEQ ID NO: 3)
METGLRWLLLVAVLKGVQCQEQLEESGGDLVKPEGSLTLTCTASRFSFSS

SYWICWVRQAPGKGLEWIACIYAGDSGSSYYASWAKGRFTVSKTSSTTVT

LQTTSLTAADTATYFCARASVGAAYDYFALWGPGTLVTVSSGQPKAPSVF

PLAPCCGDTPSSTVTLGCLVKGYLPEPVTVTWNSG hTK1, Klon 6C6, light chain:
                                       (SEQ ID NO: 4)
MDTRAPTQLLGLLLLWLPGARCALVMTQTPASVEAAMGGTVTIKCQASED

VSSHLAWYQQRPGQPPKLLIYGASDLASGVPSRFTGSGSGTQFTLAISDL

ECADAATYYCQGYYYISDSPYVFGGGTEVVVKGDPVAPTVLIFPPAADQV

ATGTVTIVCVANKYFPDVTVTWEVDGTTQTTGIENSKTPQNSADCTYNLS

STLTLTSTQYNSHKEYTCKVTQGTTSVVQSFNRGDC hTK1, Klon 4H4, heavy chain:
                                       (SEQ ID NO: 7)
METGLRWLLLVAVLKGVQCQSLEESGGGLVQPEGSLTLTCTASGFSFSSG

YDMCWVRQTPGKGLEWIACISVDSDGVTYYASWAKGRFTISKTSSTTVTL

QMTSLTAADTATYFCARGYESSSGVYIPYFTLWGPGTLVTVSSGQPKAPS

VFPLAPCCGDTPSSTVTLGCLVKGYLPEPVTVTWNSG
```

-continued hTK1, Klon 4H4, light chain:
(SEQ ID NO: 8)
MDMRAPTQLLGLLLLWLPGARCADIVLTQTPASVEAAVGGTVTIKCQASQ

SIYSYLAWYQHKPGQPPKLLIYKASTLASGVPSRFKGSGSGTEYTLTISD

LECADAATYYCQHYYYSSTSGGGVFGGGTEVVVKGDPVAPTVLIFPPAAD

QVATGTVTIVCVANKYFPDVTVTWEVDGTTQTTGIENSKTPQNSADCTYN

LSSTLTLTSTQYNSHKEYTCKVTQGTTSVVQSFNRGDC hTK1, Klon 23C11, heavy chain:
(SEQ ID NO: 9)
METGLRWLLLVAVLKGVQCQSLEESGGRLVTPGTPLTLTCTASGFSLSNY

YMSWVRQAPGKGLEWIGIIYGDDNTYCANWTKGRFTISKTSTTVDLTITS

PTTEDTATYFCARGPDYIAAKMDIWGPGTLVTVSLGQPKAPSVFPLAPCC

GDTPSSTVTLGCLVKGYLPEPVTVTWNSG hTK1, Klon 23C11, light chain:
(SEQ ID NO: 10)
MDTRAPTQLLGLLLLWLPGARCDVVMTQTPASVEAAVGGTVTIKCQASQS

ISGYLSWYQQKPGQRPKLLIYRASTLESGVPSRFKGSGSGTEFTLTISDL

ECADAATYYCQCTYGSSTFSSYGNAFGGGTEVVVKGDPVAPTVLIFPPAA

DQVATGTVTIVCVANKYFPDVTVTWEVDGTTQTTGIENSKTPQNSADCTY

NLSSTLTLTSTQYNSHKEYTCKVTQGTTSVVQSFNRGDC

As obvious full length immunoglobulins or any binding fragments thereof—if desired/required—can be easily construed by any person of skill in the art based on sequences disclosed above.

Example 3: Epitope Characterization

As described in Example 2, four different monoclonal antibodies could be generated that exhibit the required binding properties needed for them to be of utility in an immunoassay development.

In a first attempt to characterize the epitope bound by the newly generated antibodies a PepScan analysis was performed. For this analysis synthetic peptides, consisting of 15 amino acids each, each shifted by 1 amino acids (1-15: 2-16, etc.) and spanning the entire sequence of hTK-1 (SEQ ID NO:1) were synthesized. These PepScan peptides were spotted onto microscope slides. After blocking for non-specific binding cell culture supernatant of the various MABs was incubated on the microscope slides. Unbound MAB was washed off and bound MAB was detected by use of HRP—labeled goat anti-rabbit IgG according to a routine method.

Only one of the four MABs (antibody 4H11) obtained by the method of Example 2 did react with a linear epitope. As could be shown the epitope bound by this antibody is comprised in the sequence spanning amino acid residues 211 through 230 of hTK-1 (SEQ ID NO: 6).

Polyclonal as well as monoclonal antibodies reacting with a synthetic peptide corresponding to a polypeptide consisting of amino acids 194 through 225 of hTK-1 (SEQ ID NO:2) are known in the prior art, see e.g. WO 2015/094106. The three MABs 4H4; 6C6; and 23C11, respectively, did not bind to a polypeptide consisting of amino acids 194 through 225 of hTK-1 (SEQ ID NO:2) nor did they show significant binding to any of the PepScan peptides tested. This indicates that these three MABs all bind to a conformation dependent epitope on hTK-1. As these three MABs from the very beginning looked quite promising for further assay development, additional efforts were made in order to gain more knowledge on the epitope bound by these three MABs.

The epitope characterization by competition experiments was performed on a GE Healthcare Biacore 4000 instrument at 25° C. A Biacore Biotin Capture Kit, Series S sensor (Cat.-No. 28-9202-34) was mounted into the instrument and was hydrodynamically addressed and preconditioned according to the manufacturer's instructions. The system buffer was HBS-N (10 mM HEPES pH 7.4, 150 mM NaCl). The sample buffer was the system buffer. The biotin capture reagent, as provided by the manufacturer GE Healthcare, was diluted 1:50 in system buffer and was injected at 10 µl/min for 60 sec over flow cells 1, 2, 3 and 4 to address the spots 1, 2 and 4, 5. Spot 3 served as a reference. 10 nM biotinylated primary antibody was injected at 30 µl/min for 120 sec contact time to address the spots 1 and 5 in all four flow cells. Spots 2 and 4 served as controls. 10 nM human recombinant thymidine kinase-1 (hTK-1, Roche, 114 kDa, tetramer) were injected at 30 µl/min into all flow cells for 180 sec contact time to address the spots 1, 2 and 4, 5. 100 nM of non-biotinylated primary antibody were again injected at 30 µl/min to address the spots 1, 2 and 4, 5 on all flow cells for 180 sec contact time in order to block remaining accessible epitopes of the primary antibody. 100 nM of secondary antibody was injected at 30 µl/min for 180 sec contact time into all flow cells to address the spots 1, 2 and 4, 5. Finally the complexes formed on the sensor surface were completely removed by a 120 sec contact time regeneration step over all flow cells and all spots using the regeneration solution as provided by the manufacturer GE Healthcare.

Four recombinant monoclonal rabbit IgG antibodies were this way investigated for their hTK-1 epitope accessibility properties: Antibody 4H11 (an antibody binding to a linear epitope on SEQ ID NO:6) and rabbit MABs 23C11, 6C6 and 4H4.

Before and after each sample injection, report points were set. The read out of the report points in Response Units [RU] was done by using the Biacore Evaluation V.1.1 software.

To the initial biotinylated primary antibody capturing signal (bi-Ab1, [RU]) the second binding response signal of the non-biotinylated primary antibody (block Ab1 [RU]) was added. The Molar Ratio Epitope Accessibility $MR_{EA}$=Ab2 [RU]/(bi-Ab1 [RU]+block Ab1 [RU]) was calculated and was used as an estimate for the epitope accessibility of the respective antibodies used in the assay.

In order to verify the tetrameric state of the hTK analyte, a second Molar Ratio was calculated from the hTK binding signal versus the capture level of the biotinylated primary antibody by using the formula MR=hTK [RU]/bi-Ab1 [RU]*Molecular Weight bi-Ab1(150 kDa)/Molecular Weight hTK (114 kDa).

For example, antibody 4H11 showed a binding stoichiometry (=Molar Ratio) antibody 4H11/hTK-1 MR of 1:1. In this biosensor assay a single, tetrameric hTK-1 molecule binds to a single antibody 4H11 molecule. Within the described antibodies, only antibody 4H11 shows a homologous hTK-1 complex formation when being used as block Ab. Therefore, a sandwich assay would be possible by using a sequential assay protocol using antibody 4H11 twice. No homologous complex formation could be detected for the rabbit monoclonal antibodies MABs 23C11, 6C6 and 4H4. This means that MABs 23C11, 6C6 and 4H4 bind to the same epitope region. Antibodies 23C11, 6C6 and 4H4 form a sandwich with antibody 4H11 as secondary antibody. According to this assay the best performing sandwich pair is 6C6 as biotinylated primary antibody, which forms a complex with antibody 4H11 showing a Molar Ratio $MR_{EA}=0.4$, which means 40% epitope accessibility on the hTK analyte.

As obvious from the table shown below, the antibody 4H11 (binding to a C-terminal linear epitope comprised in SEQ ID NO:6) is able to form immuno complexes with 23C11, 6C6 and 4H4. On the other hand it is clear that the rabbit monoclonal antibodies MABs 23C11, 6C6 and 4H4 share the same epitope.

TABLE 1

Epitope Accessibility Matrix

| biotinylated primary antibodies | secondary antibodies | | | |
|---|---|---|---|---|
| | 4H11-IgG | 23C11-IgG | 6C6-IgG | 4H4-IgG |
| 4H11-IgG | 0.1 | 0.1 | 0.1 | 0.1 |
| 23C11-IgG | 0.2 | 0.0 | 0.0 | 0.0 |
| 6C6-IgG | 0.4 | 0.0 | 0.0 | 0.0 |
| 4H4-IgG | 0.2 | 0.0 | 0.0 | 0.0 |

Shown is the sandwich formation of four anti-hTK-1 antibodies using recombinant h-TK-1 as an analyte in solution. A value of 0.0 in the table indicates that the first and the second antibody used bind to the same epitope. A value of 0.1 or higher indicates sandwich formation, despite the intermediate blocking step, i.e. the two antibodies investigated bind to different epitopes.

Example 4: Production of the Mab-Conjugates for Use in Elecsys Immunoassay Experiments In brief, the following procedures/steps were carried out in order to obtain the antibody conjugates for the capture and detection sides of the immunological assay.

Cell culture supernatant (the recombinant antibodies comprised therein) as obtained from the by B-cell PCR generated cells (see above) was used as a starting material.

The recombinant antibody comprised in the tissue culture supernatant was purified by affinity chromatography to protein A.

An antibody used as a capture antibody was cleaved to the F(ab')2 fragment with pepsin and the F(ab')2 fragment further purified by affinity chromatography and size-exclusion chromatography. The F(ab')2 fragment was then reduced to Fab' and site-specific biotinylated via thiol-chemistry, thereby obtaining a mono-biotinylated Fab'-fragment.

An antibody used as a detection antibody was chemically conjugated to sulfo-Ruthenium (WO 2003/002974) by use of a sulfo-BPRu NHS Ester (=CAS Reg. Number 482618-42-8 also known in the art as ruthenate(2-), bis[[2,2'-bipyridine]-4,4'-dimethanesulfonato(2-)-κN$^{1'}$][1-[4-(4'-methyl[2,2'-bipyridin]-4-yl-κN$^1$, κN$^{1'}$)-1-oxobutoxy]-2,5-pyrrolidinedione]-, sodium (1:2), (OC-6-31)) and unbound label was removed by size-exclusion chromatography.

Example 5: Samples and Htk-1 Measurements

5.1 Samples

A "black-and-white" panel was investigated. On the one hand serum samples from 50 (for some experiments only 49 were still available) healthy donors have been used for quantification of hTK-1 in various assays. On the other hand, hTK-1 was measured in 48 (for some experiments only 47 were still available) samples from patients with diffuse large B-cell lymphoma (DLBCL).

5.2 Prototype Electrochemiluminescence Immunoassays

Based on the monoclonal rabbit antibodies obtained as described in Example 3, purified and conjugated as described in Example 4, respectively, several prototype immunoassays have been established.

The typical set-up of a prototype electrochemiluminescent immunoassay makes use of biotinylated capture antibody (or an antigen binding fragment thereof) and a detection antibody (or an antigen binding fragment thereof) which is labeled with a ruthenium complex.

Immunoassay data in most cases were generated using a conventional Fab' fragment that was biotinylated according to conventional procedures. Measurements were carried out in a sandwich assay format on a cobas® E170 analyzer from Roche. Signal detection in the cobas® E170 analyzer is based on electrochemiluminescense. In this sandwich assay the biotin-conjugate (i.e. the capture antibody) is immobilized on the surface of a streptavidin-coated magnetic bead. The detection-antibody bears a complexed ruthenium cation as the signaling moiety. In the presence of analyte, the chromogenic ruthenium complex is bridged to the solid phase and emits light at 620 nm after excitation at the platinum electrode comprised in the measuring cell of the cobas® E170 analyzer. The signal output is in arbitrary light units.

Measurements were, e.g., performed with calibrators spiked with recombinant hTK-1 from HEK-cells as well as with the human serum samples mentioned above.

The experimental hTK-1 assay was conducted as follows. 25 µl of human serum sample or of spiked calibrator, 25 µl of pretreatment reagent (comprising 10 mM DTBA) were mixed an incubated for 9 minutes; thereafter 60 µl of capture antibody-biotin conjugate and 60 µl of detection antibody ruthenium label conjugate were incubated together for another 9 minutes followed by the addition of 30 µl streptavidin-coated paramagnetic microparticles. The final mixture was incubated for further 9 minutes. Afterwards, the hTK-1 was detected as usual (i.e. via the electrochemiluminescent signal generated in these experiments).

Interestingly, each of the MABs to a conformation dependent epitope in combination with the MAB to the C-terminus (4H11) did result in quite a good sandwich combination. I.e. each of these combinations can be used to establish a high quality immunoassay for measurement of hTK-1.

Attempts have also been made to use one and the same antibody both as capture and as detection antibody. The combination of 4H11 used as a biotinylated capture and as a ruthenylated detection antibody did yield quite low signal counts, i.e. no satisfactory results. Surprisingly the antibodies to the conformation dependent epitope if used as a biotinylated capture and as a ruthenylated detection antibody did yield high but somewhat lower signal counts as a combination of one antibody to a linear epitope (4H11) with any one of the antibodies to a conformation dependent epitope (4H4; 6C6; or 23C11).

It was also possible to use either 4H11 as a capture antibody and an antibody to a conformational epitope as a detection antibody, or change orientation of the anti-hTK-1 antibodies, i.e. to use an antibody to a conformational epitope as capture antibody and the 4H11 antibody as detection antibody.

Below given are the results obtained for a) the combination of biotinylated 4H11 (used as Fab'-Bi) with ruthenylated 23C11(used as IgG) and b) biotinylated 6C6 (used as Fab'-Bi) with ruthenylated 4H11 (used as IgG).

Calibration results for both prototype a) and b, respectively, are given in Table 2 below.

TABLE 2

Measurement of hTK-1 with the two assay prototypes

| [hTk-1] in ng/mL | TK1: Prototype A) 4H11-Fab'-Bi: 23C11-IgG-suBPRu | | | TK1: Prototype B) 6C6-Fab'-Bi: 4H11-IgG-suBPRu | | |
|---|---|---|---|---|---|---|
| | Counts | Conc | $MW_{conc}$ | Counts | Conc | $MW_{conc}$ |
| 0.0000 | 1859 | 0.0000 | 0.0000 | 1837 | 0.0000 | 0.0000 |
| | 1860 | 0.0000 | | 1826 | 0.0000 | |
| 1.00 | 31481 | 1.27 | 1.28 | 30193 | 1.30 | 1.30 |
| | 31738 | 1.29 | | 30103 | 1.30 | |
| 5.00 | 110634 | 4.90 | 4.91 | 105843 | 4.92 | 4.91 |
| | 110983 | 4.92 | | 105452 | 4.90 | |
| 10.0 | 212023 | 9.69 | 9.63 | 198859 | 9.47 | 9.60 |
| | 209206 | 9.56 | | 204252 | 9.73 | |
| 100 | 2013189 | 101 | 100 | 1960303 | 99.5 | 100 |
| | 2008135 | 100 | | 1994291 | 101 | |

In Table 2 signals obtained in the two different immunoassay prototypes using various amounts of recombinant hTK-1 as analyte are given. Double measurements have been performed. As can be seen both assay prototypes give very good results in terms of concordance of double determinations/Counts and concentration (=conc), concentration of hTK-1 calculated/found (MW conc) and overall signal magnitude.

Figure 1:
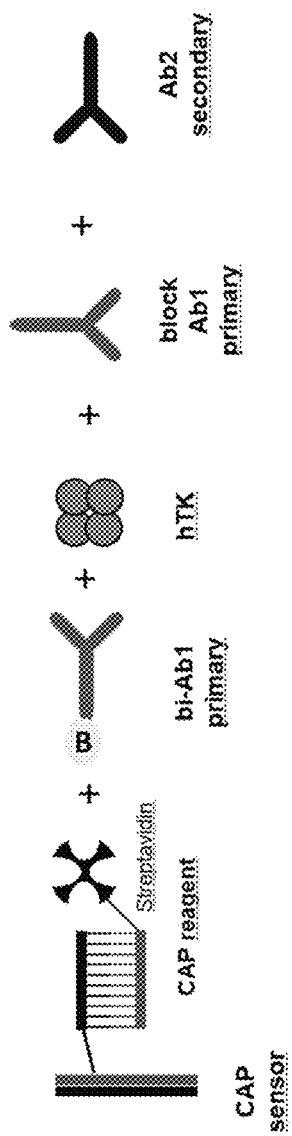
FIG. 1: Schematic representation of the Biacore assay configuration used to determine the hTK-1 epitope accessibility. The sequence of the various incubation steps is depicted.
Figure 2:
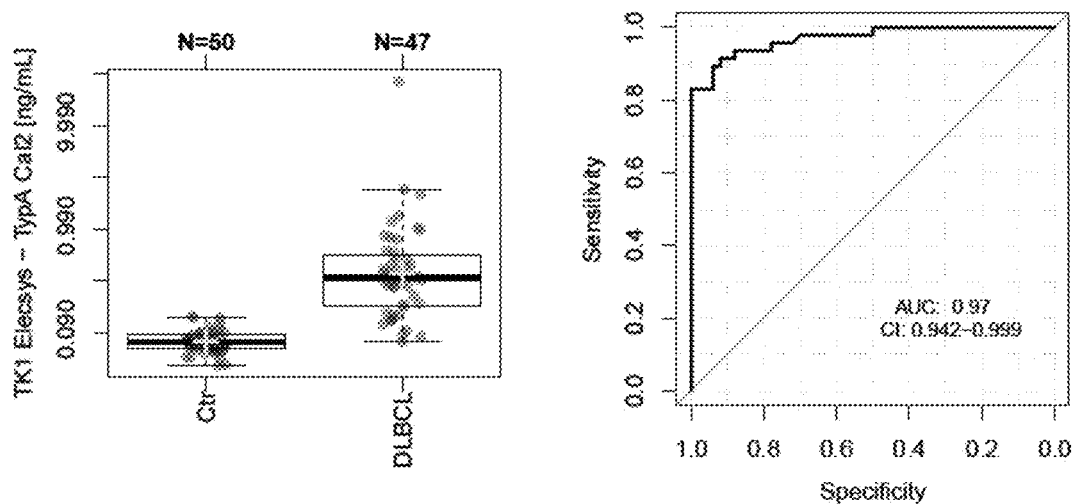
FIGS. 2A and 2B: Graphical representation of the immuno assay data obtained with prototype A) (=FIG. 2A) and prototype B) (=FIG. 2B), respectively. In the left hand part of FIG. 2A and FIG. 2B, respectively, Box-Whisker-Plots (Boxplots) are given. On the y-axis (in log scale) the concentration in ng/ml is shown. In the right hand part of both these Figures the area under the curve (AUC) is shown. (Abbreviations: Ctr=control samples; DLBCL=samples from patients with diffuse large B-cell lymphoma).
Figure 2:
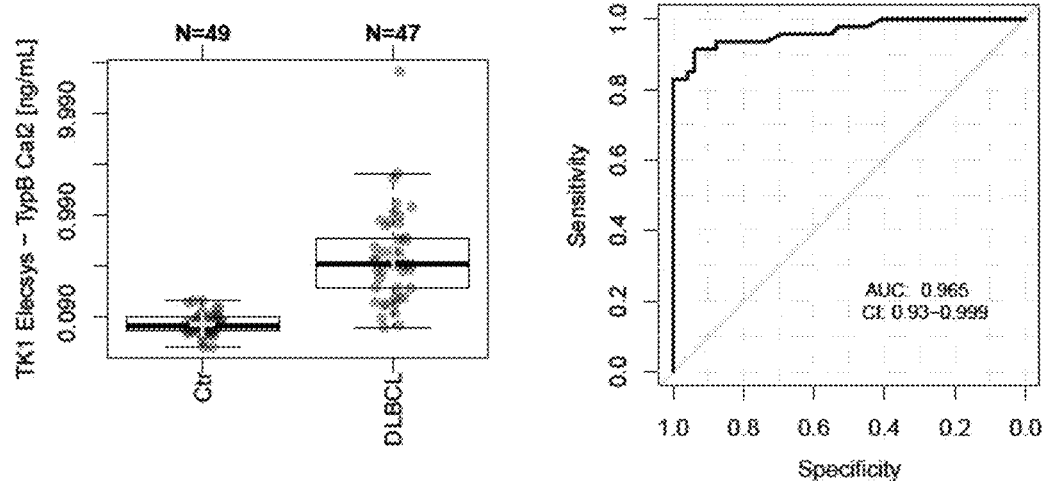

In both prototype assays the black and white panel was measured. Box-Whisker-Plots have been calculated, the receiver-operator-characteristic (ROC) has been analyzed and the area under the curve (AUC) was determined. For the assay of prototype a) the AUC was 0.971 and for the assay of prototype b) almost the same with 0.965. Both Box-Whisker-Plots (BoxPlots) with the determined concentrations of hTK-1 and the AUCs are shown in FIG. 2 for both prototype assays.

5.3 DiaSorin TK1 Activity Assay

The LIAISON® Thymidine Kinase assay, manufactured by DiaSorin, is an indirect, modified two-step, competitive chemiluminescence immunoassay (CLIA) for the quantitative determination of TK in human serum and EDTA plasma. The LIAISON® Thymidine Kinase assay was performed according to the instructions given by the manufacturer with 50 control samples and 48 samples from patients with DLBCL. It utilizes an initial enzymatic reaction in which TK in the sample converts AZT (3'-azido-3'-deoxythymidine) to AZTMP (3'-azido-3'-deoxythymidine mono phosphate), this is followed by a competitive immunoassay for the quantitative determination of AZTMP. The amount of AZT converted to AZTMP is a measure of the amount of TK present in the sample. In the assay, 50 μL of sample is incubated with 100 μL of Assay Buffer 1, 20 μL of Assay Buffer 2, and 20 μL of paramagnetic particles coated with anti-AZTMP polyclonal antibody. Rabbit anti-goat IgG, then anti-AZTMP goat polyclonal is coated to the solid phase. This is incubated for 40 minutes and then 100 μl of tracer, an AZTMP analogue conjugated to an isoluminol derivative is added. During the first incubation, AZTMP binds to the solid phase. In the second incubation, the tracer conjugate competes for binding with the AZTMP in the solution. After a 20 minute incubation, the unbound material is removed with a wash cycle. The starter reagents are then added and a flash chemiluminescent reaction is initiated. The light signal is measured by a photomultiplier as relative light units (RLU) and is proportional to the concentration of TK present in calibrators, controls, or samples.

Figure 3:
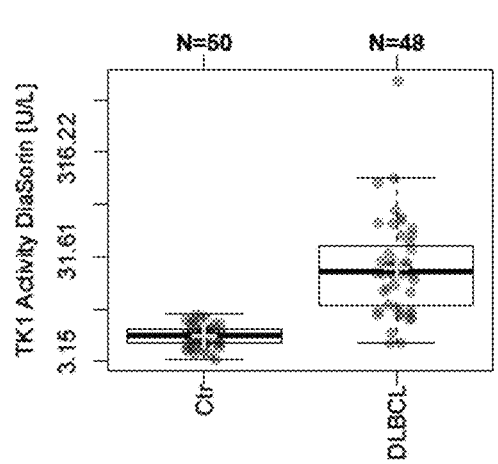
FIG. 3: Graphical representation of the LIAISON® Thymidine Kinase (activity) assay data. In the left hand part of FIG. 3 Box-Whisker-Plots (Boxplots) with units per ml on the y-axis (in log scale) are given. In the right hand part of this Figure the area under the curve (AUC) is shown. (Abbreviations: Ctr=control samples; DLBCL=samples from patients with diffuse large B-cell lymphoma).
Figure 3:
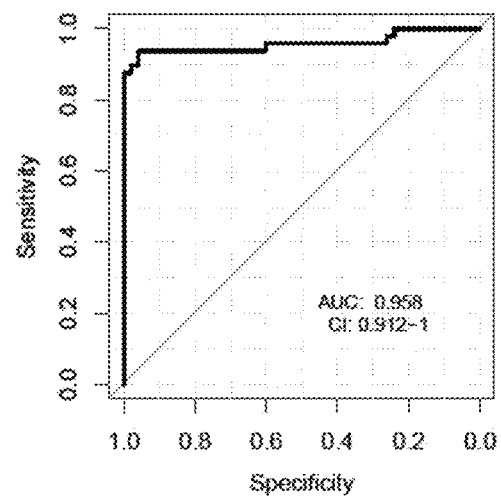

Box-Whisker-Plots have been calculated, the receiver-operator-characteristic (ROC) has been analyzed and the area under the curve (AUC) was determined. For LIAISON® Thymidine Kinase assay the AUC was found to be 0.958. Both Box-Whisker-Plot (Boxplot) and the AUC are shown in FIG. 3.

Example 6: Comparison of Tk-1 Values as Determined with Activity Assay/Immunoassay The values obtained with LIAISON® Thymidine Kinase assay on the one hand and the two prototype immunoassays on the other hand were compared to each other. Taking into account that one assay measure thymidine kinase activity while the two other measure the amount of immunoreactive hTK-1 a surprisingly high correlation (in the range of 0.95 or even above-dependent on the statistical method used) between the two different assays was found. The good correlation between these different assays for hTK-1 is also quite obvious from FIG. 4.

The invention claimed is:

1. A monoclonal antibody that specifically binds to human thymidine kinase 1 (hTK-1; SEQ ID NO:1) the antibody being characterized in that it
    a) binds to a conformation dependent epitope of hTK-1,
    b) does not bind to a polypeptide consisting of amino acids 194 through 225 of hTK-1 (SEQ ID NO:2), and
    c) does not bind to any polypeptide consisting of 15 consecutive amino acids of hTK-1.

2. The monoclonal antibody according to claim 1, having a binding affinity to hTK-1 of $10^{-9}$ Mol or better.

3. The antibody according to claim 1, further characterized in that in competes for binding to hTK-1 with an antibody or an antigen binding fragment thereof having a heavy chain variable domain of SEQ ID NO:3 and a light chain variable domain of SEQ ID NO:4.

4. An in vitro method for quantifying hTK-1, the method comprising
    a) incubating a sample in which hTK-1 shall be quantified with the antibody of claim 1, thereby generating a complex between the antibody and hTK-1,
    b) quantifying the complex formed in step a), thereby quantifying hTK-1.

5. An in vitro method for quantifying hTK-1, the method comprising
    a) incubating a sample in which hTK-1 shall be quantified with a first antibody which is an antibody of claim 1, and a second antibody to hTK-1, thereby generating a sandwich complex between the first antibody, hTK-1 and the second antibody,
    b) quantifying the sandwich complex formed in step a), thereby quantifying hTK-1.

6. An in vitro method for quantifying hTK-1, the method comprising
    a) incubating a sample in which hTK-1 shall be quantified with a pre-treatment solution comprising a reducing agent and ATP,
    b) incubating the pre-treated sample obtained in step a) with an antibody according to claim 1, thereby generating a complex between the antibody and hTK-1,
    c) quantifying the complex formed in step b), thereby quantifying hTK-1.

7. An in vitro method for quantifying hTK-1, the method comprising
    a) incubating a sample in which hTK-1 shall be quantified with a pre-treatment solution comprising a reducing agent and ATP,
    b) incubating the pre-treated sample obtained in step a) with a first antibody which is an antibody of claim 1, and a second antibody to hTK-1, thereby generating a sandwich complex between the first antibody, hTK-1 and the second antibody,
    c) quantifying the sandwich complex formed in step b), and thereby quantifying hTK-1.

8. The method according to claim 5, wherein either a first or a second antibody is bound to a solid phase or capable of binding to a solid phase and wherein either a second or a first antibody is detectably labeled.

9. The antibody of claim 1, wherein said antibody has been obtained by B-cell PCR technology.

10. The antibody of claim 1, wherein the antibody comprises an amino acid sequence selected from the group consisting of SEQ ID NOs: 3, 4, 7, 8, 9 and 10.

11. The antibody of claim 1, wherein the antibody comprises a heavy chain variable domain having an amino acid sequence selected from the group consisting of SEQ ID NOs: 3, 5, and 9.

12. The antibody of claim 1, wherein the antibody comprises a light chain variable domain having an amino acid sequence selected from the group consisting of SEQ ID NOs: 4, 6, and 10.

13. The antibody of claim 1, wherein the antibody comprises a heavy chain variable domain of SEQ ID NO:3 and a light chain variable domain of SEQ ID NO:4.

14. The antibody of claim 1, wherein the antibody comprises a heavy chain variable domain of SEQ ID NO:7 and a light chain variable domain of SEQ ID NO:8.

15. The antibody of claim 1, wherein the antibody comprises a heavy chain variable domain of SEQ ID NO: 9 and a light chain variable domain of SEQ ID NO:10.

16. The method according to claim 6, wherein the pretreatment solution comprises from 2 mM to 20 mM ATP.

17. The method according to claim 7, wherein either a first or a second antibody is bound to a solid phase or capable of binding to a solid phase and wherein either a second or a first antibody is detectably labeled.

18. The method according to claim 5, wherein the solid phase comprises paramagnetic streptavidin-coated microparticles.

19. The method according to claim 17 wherein the solid phase comprises paramagnetic streptavidin-coated microparticles.

* * * * *

SEQUENCE LISTING

```
<160> NUMBER OF SEQ ID NOS: 10

<210> SEQ ID NO 1
<211> LENGTH: 234
<212> TYPE: PRT
<213> ORGANISM: Homo sapiens

<400> SEQUENCE: 1

Met Ser Cys Ile Asn Leu Pro Thr Val Leu Pro Gly Ser Pro Ser Lys
1               5                   10                  15

Thr Arg Gly Gln Ile Gln Val Ile Leu Gly Pro Met Phe Ser Gly Lys
```

```
                     20                  25                  30
Ser Thr Glu Leu Met Arg Arg Val Arg Arg Phe Gln Ile Ala Gln Tyr
                 35                  40                  45

Lys Cys Leu Val Ile Lys Tyr Ala Lys Asp Thr Arg Tyr Ser Ser Ser
 50                  55                  60

Phe Cys Thr His Asp Arg Asn Thr Met Glu Ala Leu Pro Ala Cys Leu
 65                  70                  75                  80

Leu Arg Asp Val Ala Gln Glu Ala Leu Gly Val Ala Val Ile Gly Ile
                 85                  90                  95

Asp Glu Gly Gln Phe Phe Pro Asp Ile Val Glu Phe Cys Glu Ala Met
                100                 105                 110

Ala Asn Ala Gly Lys Thr Val Ile Val Ala Ala Leu Asp Gly Thr Phe
                115                 120                 125

Gln Arg Lys Pro Phe Gly Ala Ile Leu Asn Leu Val Pro Leu Ala Glu
                130                 135                 140

Ser Val Val Lys Leu Thr Ala Val Cys Met Glu Cys Phe Arg Glu Ala
145                 150                 155                 160

Ala Tyr Thr Lys Arg Leu Gly Thr Glu Lys Glu Val Glu Val Ile Gly
                165                 170                 175

Gly Ala Asp Lys Tyr His Ser Val Cys Arg Leu Cys Tyr Phe Lys Lys
                180                 185                 190

Ala Ser Gly Gln Pro Ala Gly Pro Asp Asn Lys Glu Asn Cys Pro Val
                195                 200                 205

Pro Gly Lys Pro Gly Glu Ala Val Ala Ala Arg Lys Leu Phe Ala Pro
                210                 215                 220

Gln Gln Ile Leu Gln Cys Ser Pro Ala Asn
225                 230

<210> SEQ ID NO 2
<211> LENGTH: 31
<212> TYPE: PRT
<213> ORGANISM: Homo sapiens

<400> SEQUENCE: 2

Gly Gln Pro Ala Gly Pro Asp Asn Lys Glu Asn Cys Pro Val Pro Gly
 1               5                  10                  15

Lys Pro Gly Glu Ala Val Ala Ala Arg Lys Leu Phe Ala Pro Gln
                20                  25                  30

<210> SEQ ID NO 3
<211> LENGTH: 185
<212> TYPE: PRT
<213> ORGANISM: Unknown
<220> FEATURE:
<223> OTHER INFORMATION: rabbit MAB 6C6 heavy chain

<400> SEQUENCE: 3

Met Glu Thr Gly Leu Arg Trp Leu Leu Leu Val Ala Val Leu Lys Gly
 1               5                  10                  15

Val Gln Cys Gln Glu Gln Leu Glu Glu Ser Gly Gly Asp Leu Val Lys
                20                  25                  30

Pro Glu Gly Ser Leu Thr Leu Thr Cys Thr Ala Ser Arg Phe Ser Phe
                35                  40                  45

Ser Ser Ser Tyr Trp Ile Cys Trp Val Arg Gln Ala Pro Gly Lys Gly
 50                  55                  60

Leu Glu Trp Ile Ala Cys Ile Tyr Ala Gly Asp Ser Gly Ser Ser Tyr
 65                  70                  75                  80
```

```
Tyr Ala Ser Trp Ala Lys Gly Arg Phe Thr Val Ser Lys Thr Ser Ser
                85                  90                  95

Thr Thr Val Thr Leu Gln Thr Thr Ser Leu Thr Ala Ala Asp Thr Ala
            100                 105                 110

Thr Tyr Phe Cys Ala Arg Ala Ser Val Gly Ala Ala Tyr Asp Tyr Phe
        115                 120                 125

Ala Leu Trp Gly Pro Gly Thr Leu Val Thr Val Ser Ser Gly Gln Pro
130                 135                 140

Lys Ala Pro Ser Val Phe Pro Leu Ala Pro Cys Cys Gly Asp Thr Pro
145                 150                 155                 160

Ser Ser Thr Val Thr Leu Gly Cys Leu Val Lys Gly Tyr Leu Pro Glu
                165                 170                 175

Pro Val Thr Val Thr Trp Asn Ser Gly
                180                 185
```

<210> SEQ ID NO 4
<211> LENGTH: 236
<212> TYPE: PRT
<213> ORGANISM: Unknown
<220> FEATURE:
<223> OTHER INFORMATION: rabbit MAB 6C6 light chain

<400> SEQUENCE: 4

```
Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ala Ser
            20                  25                  30

Val Glu Ala Ala Met Gly Gly Thr Val Thr Ile Lys Cys Gln Ala Ser
        35                  40                  45

Glu Asp Val Ser Ser His Leu Ala Trp Tyr Gln Gln Arg Pro Gly Gln
    50                  55                  60

Pro Pro Lys Leu Leu Ile Tyr Gly Ala Ser Asp Leu Ala Ser Gly Val
65                  70                  75                  80

Pro Ser Arg Phe Thr Gly Ser Gly Ser Gly Thr Gln Phe Thr Leu Ala
                85                  90                  95

Ile Ser Asp Leu Glu Cys Ala Asp Ala Ala Thr Tyr Tyr Cys Gln Gly
            100                 105                 110

Tyr Tyr Tyr Ile Ser Asp Ser Pro Tyr Val Phe Gly Gly Gly Thr Glu
        115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

<210> SEQ ID NO 5

```
<211> LENGTH: 265
<212> TYPE: PRT
<213> ORGANISM: Homo sapiens

<400> SEQUENCE: 5

Met Leu Leu Trp Pro Leu Arg Gly Trp Ala Arg Ala Leu Arg Cys
1               5                   10                  15

Phe Gly Pro Gly Ser Arg Gly Ser Pro Ala Ser Gly Pro Gly Pro Arg
                20                  25                  30

Arg Val Gln Arg Arg Ala Trp Pro Pro Asp Lys Glu Gln Glu Lys Glu
                35                  40                  45

Lys Lys Ser Val Ile Cys Val Glu Gly Asn Ile Ala Ser Gly Lys Thr
        50                  55                  60

Thr Cys Leu Glu Phe Phe Ser Asn Ala Thr Asp Val Glu Val Leu Thr
65                  70                  75                  80

Glu Pro Val Ser Lys Trp Arg Asn Val Arg Gly His Asn Pro Leu Gly
                85                  90                  95

Leu Met Tyr His Asp Ala Ser Arg Trp Gly Leu Thr Leu Gln Thr Tyr
                100                 105                 110

Val Gln Leu Thr Met Leu Asp Arg His Thr Arg Pro Gln Val Ser Ser
                115                 120                 125

Val Arg Leu Met Glu Arg Ser Ile His Ser Ala Arg Tyr Ile Phe Val
        130                 135                 140

Glu Asn Leu Tyr Arg Ser Gly Lys Met Pro Glu Val Asp Tyr Val Val
145                 150                 155                 160

Leu Ser Glu Trp Phe Asp Trp Ile Leu Arg Asn Met Asp Val Ser Val
                165                 170                 175

Asp Leu Ile Val Tyr Leu Arg Thr Asn Pro Glu Thr Cys Tyr Gln Arg
                180                 185                 190

Leu Lys Lys Arg Cys Arg Glu Glu Lys Val Ile Pro Leu Glu Tyr
        195                 200                 205

Leu Glu Ala Ile His His Leu His Glu Glu Trp Leu Ile Lys Gly Ser
        210                 215                 220

Leu Phe Pro Met Ala Ala Pro Val Leu Val Ile Glu Ala Asp His His
225                 230                 235                 240

Met Glu Arg Met Leu Glu Leu Phe Glu Gln Asn Arg Asp Arg Ile Leu
                245                 250                 255

Thr Pro Glu Asn Arg Lys His Cys Pro
                260                 265

<210> SEQ ID NO 6
<211> LENGTH: 20
<212> TYPE: PRT
<213> ORGANISM: Homo sapiens

<400> SEQUENCE: 6

Lys Pro Gly Glu Ala Val Ala Ala Arg Lys Leu Phe Ala Pro Gln Gln
1               5                   10                  15

Ile Leu Gln Cys
        20

<210> SEQ ID NO 7
<211> LENGTH: 187
<212> TYPE: PRT
<213> ORGANISM: Unknown
<220> FEATURE:
<223> OTHER INFORMATION: rabbit MAB 4H4 heavy chain
```

```
<400> SEQUENCE: 7

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Gln Pro
            20                  25                  30

Glu Gly Ser Leu Thr Leu Thr Cys Thr Ala Ser Gly Phe Ser Phe Ser
        35                  40                  45

Ser Gly Tyr Asp Met Cys Trp Val Arg Gln Thr Pro Gly Lys Gly Leu
    50                  55                  60

Glu Trp Ile Ala Cys Ile Ser Val Asp Ser Asp Gly Val Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Gly Tyr Glu Ser Ser Ser Gly Val Tyr Ile Pro
        115                 120                 125

Tyr Phe Thr Leu Trp Gly Pro Gly Thr Leu Val Thr Val Ser Ser Gly
    130                 135                 140

Gln Pro Lys Ala Pro Ser Val Phe Pro Leu Ala Pro Cys Cys Gly Asp
145                 150                 155                 160

Thr Pro Ser Ser Thr Val Thr Leu Gly Cys Leu Val Lys Gly Tyr Leu
                165                 170                 175

Pro Glu Pro Val Thr Val Thr Trp Asn Ser Gly
                180                 185

<210> SEQ ID NO 8
<211> LENGTH: 238
<212> TYPE: PRT
<213> ORGANISM: Unknown
<220> FEATURE:
<223> OTHER INFORMATION: rabbit MAB 4H4 light chain

<400> SEQUENCE: 8

Met Asp Met Arg Ala Pro Thr Gln Leu Leu Gly Leu Leu Leu Leu Trp
1               5                   10                  15

Leu Pro Gly Ala Arg Cys Ala Asp Ile Val Leu Thr Gln Thr Pro Ala
            20                  25                  30

Ser Val Glu Ala Ala Val Gly Gly Thr Val Thr Ile Lys Cys Gln Ala
        35                  40                  45

Ser Gln Ser Ile Tyr Ser Tyr Leu Ala Trp Tyr Gln His Lys Pro Gly
    50                  55                  60

Gln Pro Pro Lys Leu Leu Ile Tyr Lys Ala Ser Thr Leu Ala Ser Gly
65                  70                  75                  80

Val Pro Ser Arg Phe Lys Gly Ser Gly Ser Gly Thr Glu Tyr Thr Leu
                85                  90                  95

Thr Ile Ser Asp Leu Glu Cys Ala Asp Ala Ala Thr Tyr Tyr Cys Gln
            100                 105                 110

His Tyr Tyr Tyr Ser Ser Thr Ser Gly Gly Gly Val Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
```

-continued

```
                165                 170                 175
Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 9
<211> LENGTH: 179
<212> TYPE: PRT
<213> ORGANISM: Unknown
<220> FEATURE:
<223> OTHER INFORMATION: rabbit MAB 23C11 heavy chain

<400> SEQUENCE: 9

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Met Ser Trp Val Arg Gln Ala Pro Gly Lys Gly Leu Glu
    50                  55                  60

Trp Ile Gly Ile Ile Tyr Gly Asp Asp Asn Thr Tyr Cys Ala Asn Trp
65                  70                  75                  80

Thr Lys Gly Arg Phe Thr Ile Ser Lys Thr Ser Thr Thr Val Asp Leu
                85                  90                  95

Thr Ile Thr Ser Pro Thr Thr Glu Asp Thr Ala Thr Tyr Phe Cys Ala
            100                 105                 110

Arg Gly Pro Asp Tyr Ile Ala Ala Lys Met Asp Ile Trp Gly Pro Gly
        115                 120                 125

Thr Leu Val Thr Val Ser Leu Gly Gln Pro Lys Ala Pro Ser Val Phe
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly

<210> SEQ ID NO 10
<211> LENGTH: 239
<212> TYPE: PRT
<213> ORGANISM: Unknown
<220> FEATURE:
<223> OTHER INFORMATION: rabbit MAB 23C11 light chain

<400> SEQUENCE: 10

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Ile Ser Gly Tyr Leu Ser Trp Tyr Gln Gln Lys Pro Gly Gln
```

```
                50                  55                  60
Arg Pro Lys Leu Leu Ile Tyr Arg Ala Ser Thr Leu Glu Ser Gly Val
 65                  70                  75                  80

Pro Ser Arg Phe Lys Gly Ser Gly Ser Gly Thr Glu Phe Thr Leu Thr
                 85                  90                  95

Ile Ser Asp Leu Glu Cys Ala Asp Ala Ala Thr Tyr Tyr Cys Gln Cys
                100                 105                 110

Thr Tyr Gly Ser Ser Thr Phe Ser Ser Tyr Gly Asn Ala Phe Gly Gly
                115                 120                 125

Gly Thr Glu Val Val Val Lys Gly Asp Pro Val Ala Pro Thr Val Leu
                130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
                195                 200                 205

Thr Ser Thr Gln Tyr Asn Ser His Lys Glu Tyr Thr Cys Lys Val Thr
                210                 215                 220

Gln Gly Thr Thr Ser Val Val Gln Ser Phe Asn Arg Gly Asp Cys
225                 230                 235
```